US011409010B2

United States Patent
Li et al.

(10) Patent No.: US 11,409,010 B2
(45) Date of Patent: Aug. 9, 2022

(54) DEVICES, SYSTEMS AND METHODS FOR DETERMINING DEPTH OF INTERACTION IN POSITRON EMISSION TOMOGRAPHY DETECTORS

(71) Applicant: UIH America, Inc., Houston, TX (US)

(72) Inventors: Hongdi Li, Houston, TX (US); Aaron Rohn Selfridge, Houston, TX (US)

(73) Assignee: UIH America, Inc., Houston, TX (US)

( * ) Notice: Subject to any disclaimer, the term of this patent is extended or adjusted under 35 U.S.C. 154(b) by 0 days.

(21) Appl. No.: 17/181,770

(22) Filed: Feb. 22, 2021

(65) Prior Publication Data

US 2021/0199822 A1  Jul. 1, 2021

Related U.S. Application Data

(63) Continuation-in-part of application No. 16/528,363, filed on Jul. 31, 2019, now Pat. No. 10,962,661.
(Continued)

(30) Foreign Application Priority Data

Jan. 11, 2018  (CN) .......................... 201810027134.0

(51) Int. Cl.
*G01T 1/29* (2006.01)
*G01T 1/20* (2006.01)
(Continued)

(52) U.S. Cl.
CPC .......... *G01T 1/2985* (2013.01); *G01T 1/1642* (2013.01); *G01T 1/2018* (2013.01); *A61B 6/037* (2013.01); *A61B 6/563* (2013.01)

(58) Field of Classification Search
CPC ............................ G01T 1/1642; G01T 1/2018
See application file for complete search history.

(56) References Cited

U.S. PATENT DOCUMENTS 9,442,198 B2  9/2016  Lewellen et al.
9,513,387 B2  12/2016  Henseler et al.
(Continued)

FOREIGN PATENT DOCUMENTS

CN  101073019 B  6/2011
CN  105425270 A  3/2016

OTHER PUBLICATIONS

Chen et al., "Development of Panel Breast PET Based on Coupling of BGO and SiPM," *Chinese Journal of Biomedical Engineering*, 35(6), pp. 754-758, 2016.
(Continued)

*Primary Examiner* — Hugh Maupin
(74) *Attorney, Agent, or Firm* — Faegre Drinker Biddle & Reath LLP

(57) ABSTRACT

Methods and systems for detecting a three-dimensional position of a scintillation event converting a radiation into a light. For example, a system includes a crystal array including a plurality of crystal elements, a light sensor array including a plurality of light sensors, a first crystal pair of the plurality of crystal pairs corresponds to a first light sensor pair of the plurality of light sensor pairs; a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair.

20 Claims, 23 Drawing Sheets

Related U.S. Application Data which is a continuation-in-part of application No. 16/125,928, filed on Sep. 10, 2018, now Pat. No. 10,502,847.

(51) Int. Cl.
   *G01T 1/164* (2006.01)
   *A61B 6/00* (2006.01)
   *A61B 6/03* (2006.01)

(56) References Cited

U.S. PATENT DOCUMENTS

| | | | |
|---|---|---|---|
| 9,606,245 | B1 | 3/2017 | Czarnecki et al. |
| 9,696,439 | B2 | 7/2017 | An et al. |
| 9,864,072 | B2 | 1/2018 | Li et al. |
| 10,502,847 | B2 | 12/2019 | Li et al. |
| 10,962,661 | B2 | 3/2021 | Li et al. |
| 2009/0224164 | A1 | 9/2009 | Lewellen et al. |
| 2011/0192982 | A1 | 8/2011 | Henseler et al. |
| 2012/0061577 | A1 | 3/2012 | Oleinik et al. |
| 2012/0235047 | A1 | 9/2012 | Lewellen et al. |
| 2013/0153774 | A1 | 6/2013 | Hughes et al. |
| 2014/0138548 | A1 | 5/2014 | Li et al. |
| 2016/0170040 | A1 | 6/2016 | Kim |
| 2016/0170045 | A1 | 6/2016 | Kim |
| 2016/0223690 | A1 | 8/2016 | Uchida |
| 2017/0234990 | A1 | 8/2017 | Sowards-Emmerd et al. |
| 2017/0285182 | A1 | 10/2017 | Fu et al. |
| 2019/0353809 | A1 | 11/2019 | Li et al. |

OTHER PUBLICATIONS

European Patent Office, The Extended European Search Report in EP Application No. 19150271.5, dated Jun. 6, 2019 (10 pages).

Ge et al., "Correction Methods of Depth of Interaction in Positron Emission Tomography," *Chinese Journal of Medical Imaging Technology*, 27(10), pp. 2157-2160, 2011.

Kang et al., "A Depth-Encoding PET Detector Inserting Glass Plate Between Crystal Layers," *2011 IEEE Nuclear Science Symposium Conference Record*, pp. 2859-2864, 2011.

Kuang et al., "Progress of Small Animal PET Scanners with High Spatial Resolution and High Sensitivity," *Nuclear Physics Review*, 33(3), pp. 337-344, 2016.

Pizzichemi et al., "A New Method for Depth of Interaction Determination in PET Detectors," *Physics in Medicine & Biology*, 61, pp. 4679-4698, 2016.

Rafecas et al., "Inter-crystal Scatter in a Dual Layer, High Resolution LSO-APD Positron Emission Tomograph," *Physics in Medicine & Biology*, 48, pp. 821-848, 2003.

1600

Obtaining output information of a first photon-sensor and a second photon-sensor, the first and the second photon-sensors being optically coupled with one crystal group, the output information corresponding to a photon gamma interaction in the crystal group ~1601

↓

Identifying, in the crystal group, a target crystal element in which the photon gamma interaction occurs based on the output information ~1602

↓

Determining, based on the output information, a depth of the photon gamma interaction within the target crystal element ~1603

Obtaining output information of a plurality of photon-sensor groups, each of the plurality of photon-sensor groups including at least two photon-sensors and being optically coupled to a crystal group of a detector, the output information corresponding to a photon gamma interaction in a plurality of crystal groups ⎯⎯1701

Determining, based on the output information, a plurality of candidate positions of the photon gamma interaction in the plurality of crystal groups, each of the plurality of candidate positions corresponding to one of the plurality of crystal groups and including a candidate depth of the photon gamma interaction within the corresponding crystal group ⎯⎯1702

Determining, based on the output information, that an inter crystal scatter occurs within the plurality of crystal groups ⎯⎯1703

Designating, among the plurality of candidate positions, the candidate position with the smallest candidate depth as a position of the photon gamma interaction ⎯⎯1704

FIG. 17

DEVICES, SYSTEMS AND METHODS FOR DETERMINING DEPTH OF INTERACTION IN POSITRON EMISSION TOMOGRAPHY DETECTORS

CROSS-REFERENCES TO RELATED APPLICATIONS

This application is a continuation-in-part of U.S. patent application Ser. No. 16/528,363, filed on Jul. 31, 2019, which is a continuation-in-part of U.S. patent application Ser. No. 16/125,928, filed on Sep. 10, 2018, which claims priority to Chinese Patent Application No. 201810027134.0, filed on Jan. 11, 2018, all applications being incorporated by reference herein for all purposes.

TECHNICAL FIELD

The present disclosure generally relates to Positron Emission Tomography (PET), and more specifically, to systems and methods for determining a depth of interaction (DOI) in PET detectors.

BACKGROUND

PET is usually an imaging technique that produces a three-dimensional image of functional processes in an object or a portion thereof to monitor in vivo biologically active molecules labeled by radioactive tracers. The tracer may undergo positron emission decay and emit a positron. The positron may annihilate with an electron, generating a pair of annihilation photons (e.g., gamma photons) that move in approximately opposite directions. The annihilation photons may be absorbed by a plurality of crystal elements (e.g., arranged in the form of one or more rings) that create bursts of optical photons (e.g., visible light photons) that, in turn, may be detected by photodetectors. Then the three-dimensional image of the object may be generated based on coincident photon detections. Because pairs of detected annihilation photons may travel along nearly straight lines (referred to as lines of response (LOR)), the tracer location may be determined by identifying LORs.

In conventional systems, a PET scanner exhibits a progressive reduction in spatial resolution with increased distance away from the center of its field of view (FOV). This resolution loss is at least partly caused by an uncertainty in assigning a LOR to a detected coincident event. The uncertainty of LOR assignment may be relatively smaller for a pair of detector modules located near the scanner's central axis (i.e., an axis along an axial direction of the scanner passing through the center of the FOV) than that located far from the central axis. Also, the uncertainty of LOR assignment may be relatively smaller for a pair of detector modules located closer to each other along the axial direction of the scanner than a pair of detector modules located far away from each other. For example, as illustrated in FIG. 2a, a pair of detector modules 201 and 202 is located nearer to the scanner's center axis than a pair of detector modules 203 and 204. As illustrated in FIG. 2b, the distance between the detector modules 201 and 202 along the axial direction of the scanner is smaller than that between a pair of detector modules 202 and 205. The dotted lines A and B define a range of possible LORs assigned to the detector modules 201 and 202, C and D define a range of possible LORs assigned to the detector modules 203 and 204, and E and F define a range of possible LORs assigned to the detector modules 202 and 205. The difference $\Delta r1$ between A and B is smaller than the difference $\Delta r2$ between C and D, suggesting a relative smaller resolution loss in detector modules 201 and 202 than detector modules 203 and 204. Similarly, the difference $\Delta r1$ is smaller than the difference $\Delta r3$ between E and F, suggesting a relative smaller resolution loss in detector modules 201 and 202 than detector modules 202 and 205.

Thus, in order to improve imaging resolution, it is desirable to determine the position or depth of photon gamma interactions occurred within a PET detector. PET imaging systems that provide depth of interaction (DOI) information can assign LORs to coincident events more accurately, thereby resulting in a more uniform resolution throughout the FOV. A plurality of techniques for extracting DOI information from a PET detector has been proposed. A possible way is to optically couple photon-sensors to both ends of a crystal element of a PET detector. For example, as illustrated in FIG. 3a, a photon-sensor 301a and a photon-sensor 301b are optically coupled to two ends of a crystal element 302, respectively. The DOI information of a photon gamma interaction (e.g., a photon gamma interaction 1) within the crystal element 302 may be determined based on the ratio of output energies from the photon-sensors 301a and 301b.

Another exemplary way employs a photon-sensor array coupled to a monolithic crystal. For example, as illustrated in FIG. 3b, a photon-sensor array 303 including a plurality of photon-sensors 301c is optically coupled to a crystal element 304. The DOI information of photon gamma interaction (e.g., a photon gamma interaction 2 or 3) may be determined based on a distribution of outputs of the photon-sensors 301c. For example, when a photon gamma interaction excites one or more photons that are detected by more photon-sensors 301c, it may occur at a position farther away from the photon-sensor array 303.

Yet another exemplary way is based on multilayer crystals optically coupled with a photon-sensor array, and to determine the DOI information based on the characteristics of signals detected by the photon-sensor array. For example, as shown in FIG. 3c, a PET detector includes a first crystal layer 305, a second crystal layer 306, and a photon-sensor array 307 optically coupled to the second crystal layer 306. The properties of the crystals in different layers may be different. The above mentioned techniques may be applied in DOI determination, however, most of them rely on additional detector electronics, thereby requiring considerably more complicated hardware and possibly introducing other issues. Therefore, it is desirable to provide devices, systems, and methods for determining DOI in PET systems efficiently and accurately.

BRIEF SUMMARY OF THE DISCLOSURE

In various embodiments, a system for detecting a three-dimensional position of a scintillation event converting a radiation into light includes: a crystal array including a plurality of crystal elements arranged at least along a first direction and a second direction, the plurality of crystal elements extending along a third direction between a first end and a second end, the crystal array including a plurality of light bridges at the second end and a plurality of light tunnels at the first end; and a light sensor array including a plurality of light sensors arranged at least along the first direction and the second direction. In some examples, the plurality of crystal elements is arranged into a plurality of crystal pairs; each of the plurality of crystal pairs optically coupled to one light bridge of the plurality of light bridges at the second end extending and bridging light along the first direction; each of the plurality of crystal pairs includes two crystal elements; and the two crystal elements in each crystal pair are arranged side-by-side along the first direction and optically coupled for the light along the first direction through the one light bridge coupled to each crystal pair. In some examples, the plurality of light sensors is arranged into a plurality of light sensor pairs at the first end and configured to detect light converted from the radiation entered from the second end; each of the plurality of light sensor pairs includes two light sensors; and the two light sensors in each light sensor pair are arranged side-by-side along the first direction. In some examples, a first crystal pair of the plurality of crystal pairs corresponds to a first light sensor pair of the plurality of light sensor pairs; a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair.

In various embodiments, a system for detecting one or more three-dimensional positions of one or more scintillation events for converting a radiation into light includes: a crystal array including: a plurality of crystal elements arranged in crystal rows along a first direction and in crystal columns along a second direction, the plurality of crystal elements extending along a third direction between a first end and a second end; and a plurality of light bridges at the second end and a plurality of light tunnels at the first end; and a light sensor array including a plurality of light sensors arranged in light sensor rows along the first direction and in light sensor columns along the second direction, the plurality of light sensors arranged at the first end and configured to detect light converted from the radiation entered from the second end. In some examples, each crystal row of the crystal rows includes one or more crystal pairs along the first direction; each crystal pair of the one or more crystal pairs optically coupled to one light bridge of the plurality of light bridges at the second end extending and bridging light along the first direction each crystal pair of the one or more crystal pairs includes a first crystal element and a second crystal element; the first crystal element and the second crystal element are optically coupled for the light along the first direction through the one light bridge coupled to each crystal pair; each light sensor row of the light sensor rows includes one or more light sensor pairs along the first direction; each light sensor pair of the one or more light sensor pairs includes a first light sensor and a second light sensor. In some examples, each light sensor pair is configured to: determine whether the scintillation event occurs within the first crystal element or within the second crystal element; and determine the position of the scintillation event along the third direction. In some examples, a first crystal pair of the one or more crystal pairs corresponds to a first light sensor pair of the one or more light sensor pairs; a second crystal pair of the one or more crystal pairs corresponds to a second light sensor pair of the one or more light sensor pairs; and a third crystal pair of the one or more crystal pairs corresponds to the first light sensor pair and the second light sensor pair such that a scintillation event in the third crystal pair is detected by both the first light sensor pair and the second light sensor pair.

In various embodiments, a system for detecting a three-dimensional position of a scintillation event converting a radiation into light includes: a crystal array including a plurality of crystal pairs arranged at least along a first direction and a second direction, each crystal pair of the plurality of crystal pairs including a first crystal element and a second crystal element, the crystal array including a plurality of light bridges at the second end and a plurality of light tunnels at the first end; and a light sensor array including a plurality of light sensor pairs at the first end and configured to detect light converted from the radiation entered from the second end. In some examples, for each crystal pair: the first crystal element and the second crystal element arranged side-by-side along the first direction; the first crystal element and the second crystal element extending along a third direction between a first end and a second end; the first crystal element and the second crystal element configured to receive the radiation entered from the second end; the crystal pair being optically coupled to one light bridge of the plurality of the light bridges at the second end extending and bridging light along the first direction; and the first crystal element and the second crystal element being optically coupled for the light along the first direction through the one light bridge. In some examples, a first crystal pair of the plurality of crystal pairs corresponds to a first light sensor pair of the plurality of light sensor pairs; a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 16 is a flowchart illustrating an exemplary process for determining the position of a photon gamma interaction in a crystal group according to some embodiments of the present disclosure.

FIG. 17 is a flowchart illustrating an exemplary process for determining the position of a photon gamma interaction according to some embodiments of the present disclosure.

DETAILED DESCRIPTION

Figure 1:
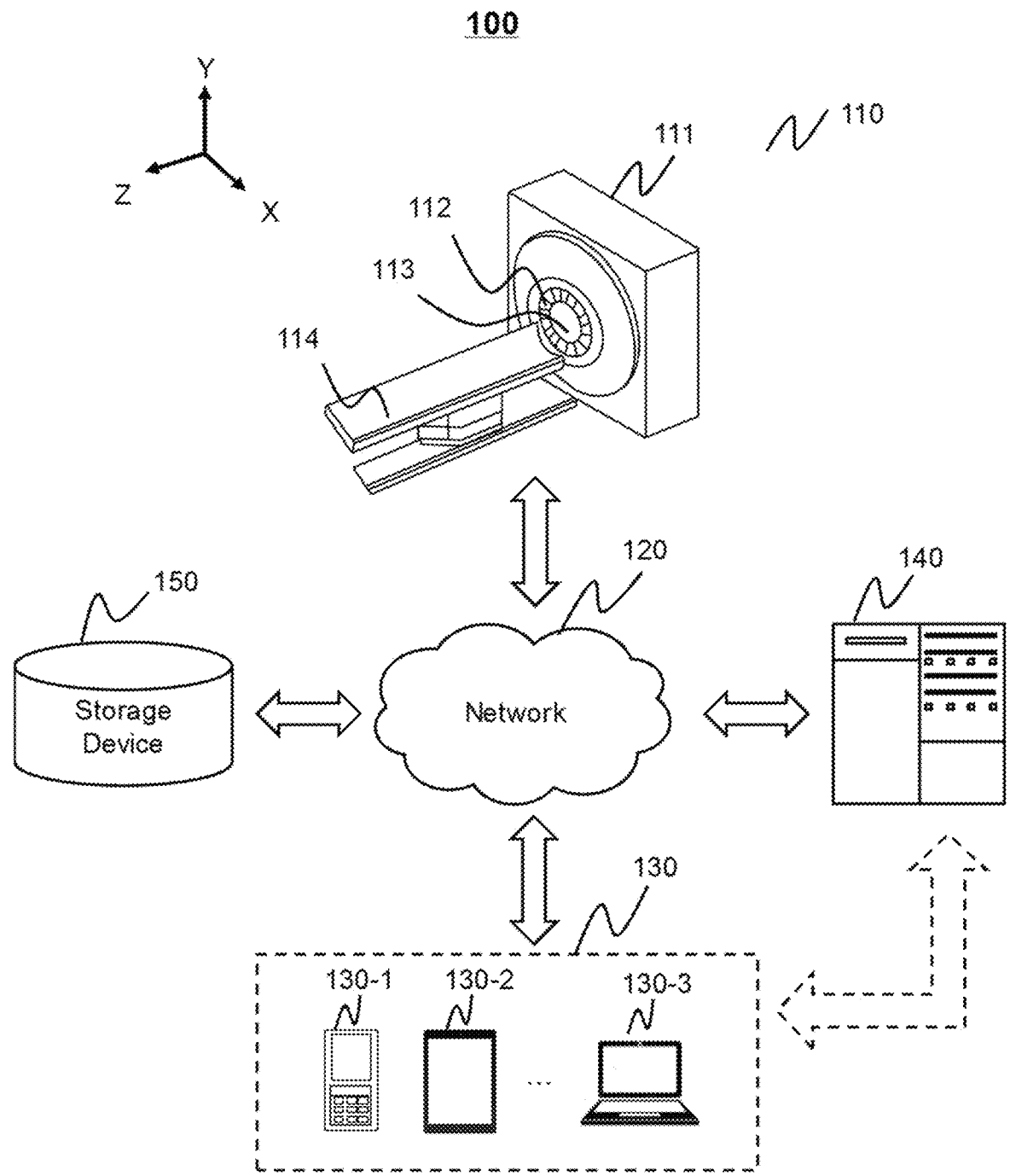
FIG. 1 is a schematic diagram illustrating an exemplary imaging system according to some embodiments of the present disclosure.
Figure 2A:
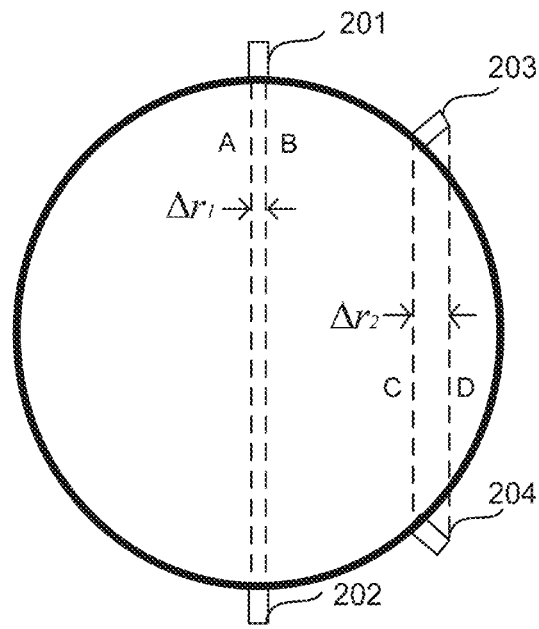
FIG. 2a is a schematic diagram illustrating a radial cross section of an exemplary PET imaging device according to some embodiments of the present disclosure.
Figure 2B:
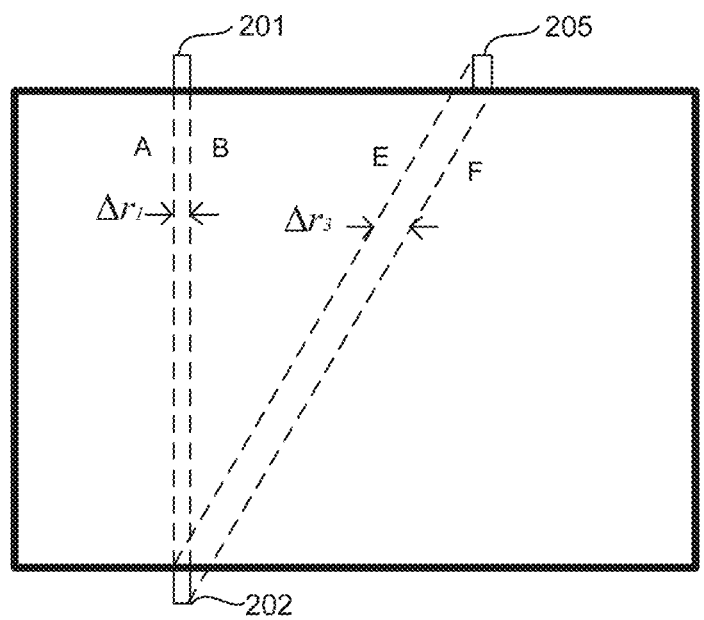
FIG. 2b is schematic diagram illustrating an axial cross section of an exemplary PET imaging device according to some embodiments of the present disclosure.
Figure 3A:
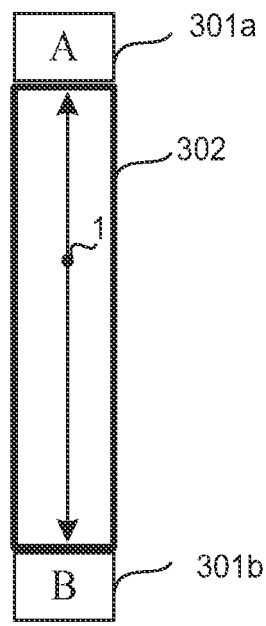
FIG. 3a is a schematic diagram illustrating an exemplary detector according to some embodiments of the present disclosure.
Figure 3B:
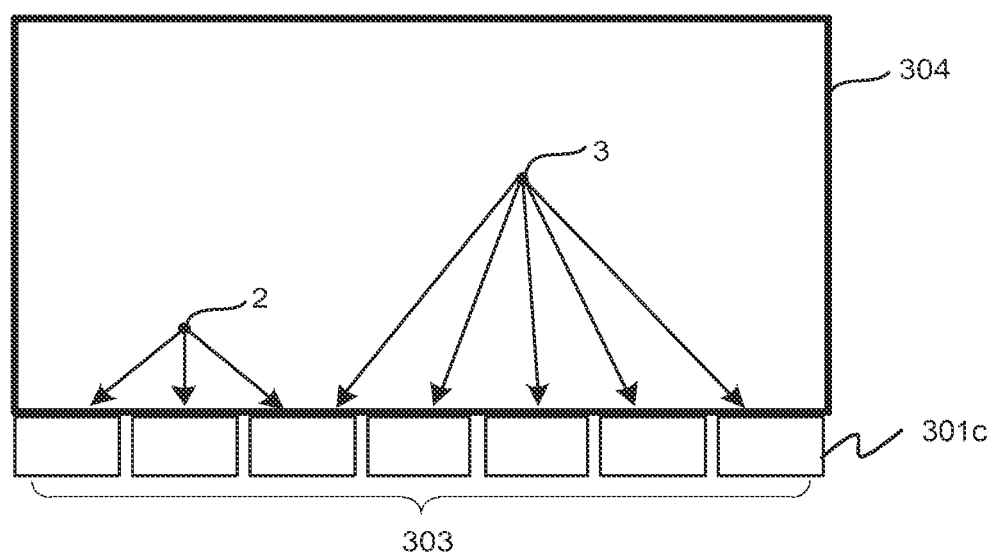
FIG. 3b is a schematic diagram illustrating an exemplary detector according to some embodiments of the present disclosure.
Figure 3C:
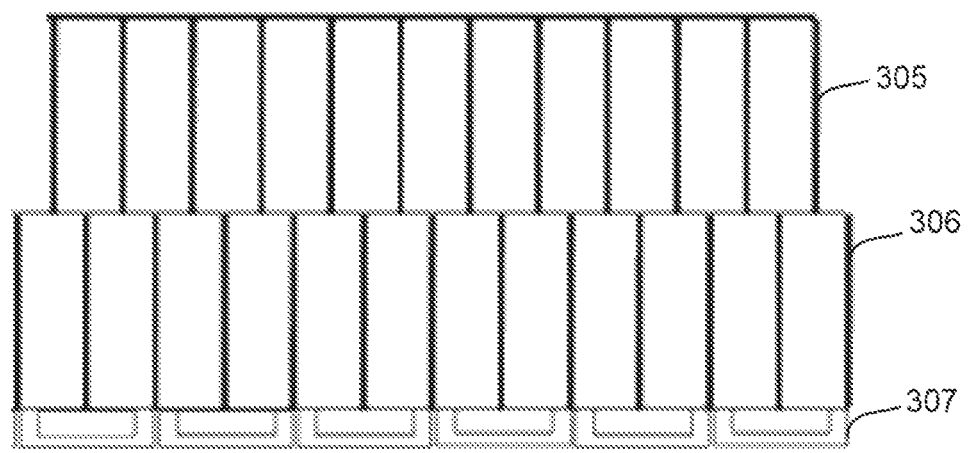
FIG. 3c is a schematic diagram illustrating an exemplary detector according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/ blocks or computing device functionality described herein may be implemented as software modules/units/blocks, but may be represented in hardware or firmware. In general, the modules/units/blocks described herein refer to logical modules/units/blocks that may be combined with other modules/ units/blocks or divided into sub-modules/sub-units/sub-blocks despite their physical organization or storage. The description may be applicable to a system, an engine, or a portion thereof.

It will be understood that the terms "ring," "layer," "element," "group," etc., when used in this disclosure, refer to one or more parts with one or more specific purposes. However, a structure that may perform a same or similar function compared to a part exemplified above or referred to elsewhere in the present disclosure may be named differently from the present disclosure.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between crystal elements) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

The present disclosure relates to devices, systems and methods for determining a position of a photon gamma interaction in a PET detector. In some embodiments, the PET detector may include a crystal array and a photon-sensor array optically coupled with the crystal array. The crystal array may include a plurality of crystal elements arranged along a first direction and a second direction, and the photon-sensor array may include a plurality of photon-sensors. The crystal elements may form a plurality of crystal groups along the first direction. The PET detector may further include a plurality of optical separators (e.g., a first optical separator, a second optical separator, a third optical separator) of the same or different lengths configured to control light transmission in the PET detector. The position of the photon gamma interaction in a crystal group may be determined based on output information of photon-sensors optically coupled with the crystal group.

FIG. 1 is a schematic diagram illustrating an exemplary imaging system 100 according to some embodiments of the present disclosure. In some embodiments, the imaging system 100 may be a single-modality system, such as a positron emission tomography (PET) imaging system. Alternatively, the imaging system 100 may be a multi-modality system, such as a PET-CT imaging system, a PET-MM imaging system, etc.

In some embodiments, the imaging system 100 may include a PET imaging device 110, a network 120, one or more terminals 130, a computing device 140, and a storage device 150. In some embodiments, the components of the imaging system 100 may be connected to each other via the network 120. Alternatively or additionally, the components of the imaging system 100 may be directly connected to each other.

The PET imaging device 110 may scan an object and generate scanning data corresponding to the object. The object may include but is not limited to one or more organs, one or more types of tissues, or the like, of a patient. In some embodiments, the PET imaging device 110 may be a medical scanning device, for example, an SPET device, a PET device, a PET-CT device, a PET-MRI device, etc. The PET imaging device 110 may include a gantry 111, a detector 112, a scanning area 113, and a table 114. An object may be placed on the table 114. The table 114 may deliver the object to a target location in the scanning area 113. The detector 112 may detect radiation rays (e.g., gamma photons) emitted from the object in the scanning area 113. In some embodiments, the detector 112 may include a plurality of detector modules. The detector modules may be arranged in a suitable configuration, including but not limited to a ring (e.g., a detector ring), a rectangle, a triangle, or an array. In some embodiments, the detector 112 may include a plurality of crystal elements, a plurality of photon-sensors, and one or more optical separators as described elsewhere in the present disclosure.

For the convenience of description, a coordinate system including an X axis, a Y axis, and a Z axis is introduced. As shown in FIG. 1, the Z axis direction may refer to a direction along which the object is moved into and out of the scanning area 113. The X axis direction and the Y axis may be perpendicular to each other, and form an x-y plane.

In application, a tracer (e.g., a radioactive isotope) may be injected into an object (via, for example, blood vessels of a patient). The atoms of the tracer may be incorporated into biologically active molecules. The molecules may gather in tissue of the patient. When a sufficient amount of the molecules are estimated to have gathered in the tissue (e.g., in an hour), the patient may be positioned on the table 114. The radioactive isotope may undergo a positron emission decay (i.e., the beta decay) and emits positrons. The positrons may interact with electrons inside the tissue (the interaction between positrons and electrons is called annihilation). The annihilations of the electrons and positrons may each produce a pair of annihilation photons that move in approximately opposite directions. When the annihilation photons strike into a crystal element of the detector 112, the annihilation photons may be absorbed by the crystal element, generating bursts of optical photons (e.g., visible light photons) that, in turn, may be detected by one or more photon-sensors. The interaction between the annihilation photons and the crystal element that produces bursts of optical photons may be referred to as a photon gamma interaction herein. The depth of the photon gamma interaction along an extension direction of the crystal element where the photon gamma interaction occurs may be referred to as a DOI.

An image may be generated by the computing device 140 based on the information associated with the annihilation photons. For example, the computing device 140 may determine the time-of-flight information associated with each of the pairs of annihilation photons. The computing device 140 may also determine DOI information based on output information of the photon-sensors in the detector 112. The computing device 140 may further determine location where the annihilation happens based on the time information and the DOI information. After the locations of annihilations are determined, the computing device 140 may generate a projection image (also referred to as a sonogram) based on the locations of the annihilations. The computing device 140 may reconstruct images based on the projection image and reconstruction techniques such as filtered back projection (FBP). The reconstructed images may indicate the tissue that contains a large number of biologically active molecules of the tracer. In some embodiments, the number of molecules of the tracer in a region may be related to biological functions of the tissues in the region. For example, if fluorodeoxyglucose (FDG) is used as the tracer in a PET scan, the number of tracer molecules in a region may be proportional to the rate of metabolism of glucose in the region. As tumors generally consume a huge amount of glucose, the region with a large number of molecules may be identified in a reconstructed image as tumor tissue.

The network 120 may include any suitable network that can facilitate the exchange of information and/or data between the components of the imaging system 100. In some embodiments, one or more components of the imaging system 100 (e.g., the PET imaging device 110, the terminal 130, the computing device 140, the storage device 150, etc.) may communicate information and/or data with one or more other components of the imaging system 100 via the network 120. For example, the computing device 140 may obtain image data (e.g., time information, energy information, DOI information) from the PET imaging device 110 via the network 120. As another example, the computing device 140 may obtain user instructions from the terminal 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof.

The terminal 130 may include a mobile apparatus 130-1, a tablet computer 130-2, a laptop computer 130-3, or the like, or any combination thereof. In some embodiments, the mobile apparatus 130-1 may include a smart home device, a wearable device, a mobile device, a virtual reality device, an augmented reality device, or the like, or any combination thereof. In some embodiments, the terminal 130 may be part of the computing device 140.

The computing device 140 may process data and/or information obtained from the PET imaging device 110, the terminal(s) 130, and/or the storage device 150. For example, the computing device 140 may process image data (including time information, energy information, DOI information, etc.) and reconstruct an image based on the image data. In some embodiments, the computing device 140 may be a single server or a server group. The server group may be centralized or distributed. In some embodiments, the computing device 140 may be local or remote. For example, the computing device 140 may access information and/or data stored in the PET imaging device 110, the terminal(s) 130, and/or the storage device 150 via the network 120. As another example, the computing device 140 may be directly connected to the PET imaging device 110, the terminal(s) 130 and/or the storage device 150 to access stored information and/or data. In some embodiments, the computing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the computing device 140, or a portion of the computing device 140 may be integrated into the PET imaging device 110.

The computing device 140 may include a processor, a storage module, an input/output (I/O) and a communication port. The processor may execute computer instructions (e.g., program code) and perform functions of the computing device 140 described herein. The computer instructions may include, for example, routines, programs, objects, components, data structures, procedures, modules, and functions, which perform particular functions described herein. The storage module may store data/information obtained from the PET imaging device 110, the terminal 130, the storage device 150, and/or any other component of the imaging system 100. In some embodiments, the storage module may include a mass storage, a removable storage, a volatile read-and-write memory, a read-only memory (ROM), or the like, or any combination thereof. The I/O may input and/or output signals, data, information, etc. In some embodiments, the I/O may enable a user interaction with the computing device 140. In some embodiments, the I/O may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. The communication port may be connected to a network (e.g., the network 120) to facilitate data communications. The communication port may establish connections between the computing device 140 and the PET imaging device 110, the terminal 130, and/or the storage device 150. The connection may be a wired connection, a wireless connection, any other communication connection that can enable data transmission and/or reception, and/or any combination of these connections.

The storage device 150 may store data, instructions, and/or any other information. In some embodiments, the storage device 150 may store data obtained from the terminal(s) 130 and/or the computing device 140. In some embodiments, the storage device 150 may store data and/or instructions that the computing device 140 may execute or use to perform exemplary methods described in the present disclosure. In some embodiments, the storage device 150 may store image data (e.g., time information, energy information, DOI information) obtained from the PET imaging device 110. In some embodiments, the storage device 150 may include a mass storage, removable storage, a volatile read-and-write memory, a read-only memory (ROM), or the like, or any combination thereof. In some embodiments, the storage device 150 may be connected to the network 120 to communicate with one or more other components of the imaging system 100 (e.g., the computing device 140, the terminal(s) 130, etc.). Alternatively or additionally, the storage device 150 may be part of the computing device 140.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. Merely by way of example, some other components may be added into the imaging system 100, such as a patient positioning unit, data acquisition electronics, power supplies, and other devices or units. However, those variations and modifications do not depart from the scope of the present disclosure.

Figure 4:
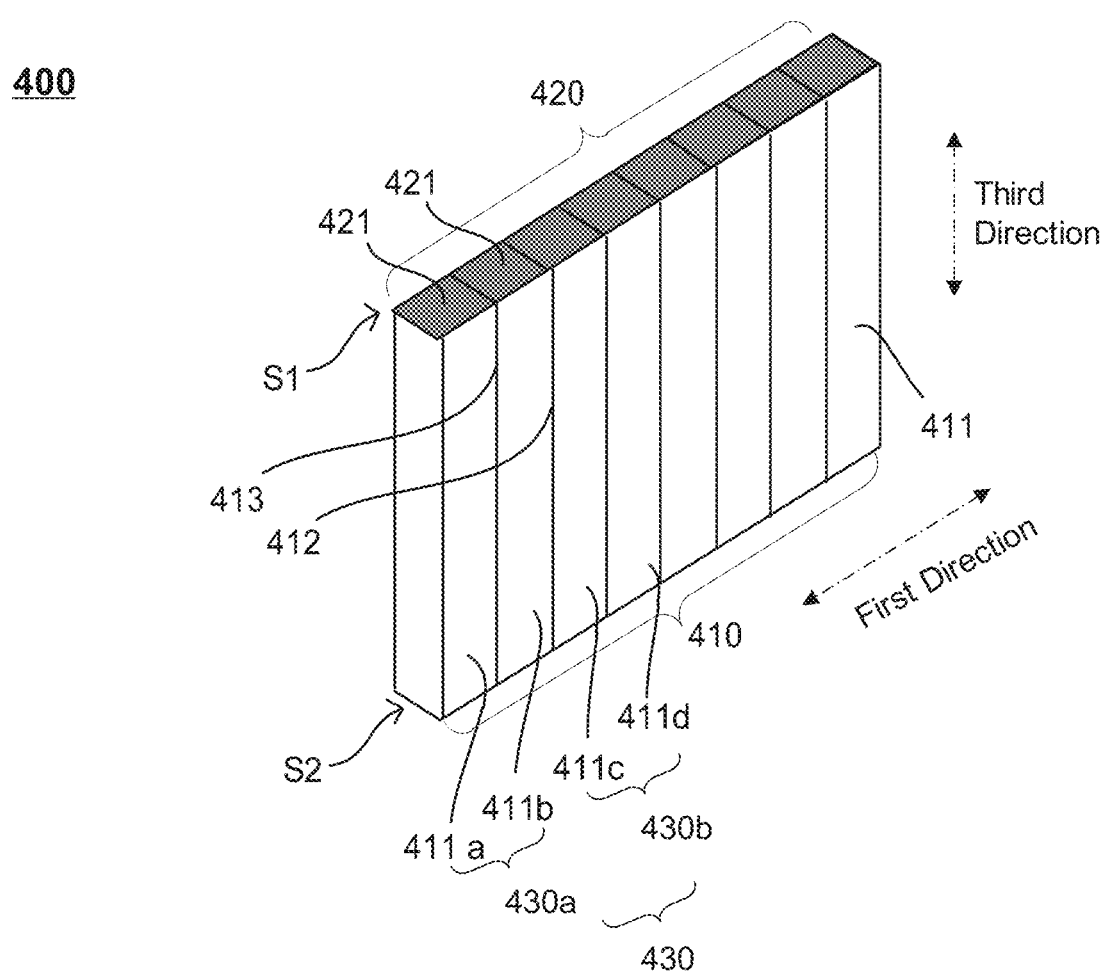
FIG. 4 is a schematic diagram illustrating an exemplary detector according to some embodiments of the present disclosure.

FIG. 4 is a schematic diagram illustrating an exemplary detector 400 according to some embodiments of the present disclosure. In some embodiments, the detector 400 may be an example of the detector 112 or a portion of the detector 112. The detector 400 may be configured to detect annihilation photons generated by annihilation events during a scan of an object.

As shown in FIG. 4, the detector 400 may include a crystal array 410, a photon-sensor array 420 optically coupled with the crystal array 410, one or more first optical separators 412, and one or more second optical separators 413. The crystal array 410 may include a plurality of crystal elements 411 (e.g., crystal elements 411a, 411b, 411c, and 411d) configured to receive annihilation photons from the object. For simplicity and illustration purposes, the crystal array 410 as illustrated includes only a row of crystal elements 411. It is not intended to be limiting. In some embodiments, the crystal array 410 may include a two-dimensional array of crystal elements. See, e.g., FIGS. 11a, 11b, and 13 and the description thereof. The photon-sensor array 420 may include a plurality of photon-sensors 421 configured to detect optical photons emitted from the first ends of the crystal elements 411.

The crystal elements 411 of the crystal array 410 may be arranged along a first direction, forming a crystal column as shown in FIG. 4. Each crystal element 411 may include a first end S1 and a second end S2 and extend along a third direction from the first end S1 to the second end S2. As used herein, the first end S1 of a crystal element 411 may refer to an end through which an optical photon exits the crystal element 411 to enter a photon-sensor 421. The second end S2 of a crystal element 411 may refer to an end through which radiation rays (e.g., gamma rays caused by annihilation events) enter the crystal element 411. The second end S2 of a crystal element 411 may be closer to the scanned object than the first end S1 of the same crystal element 411.

A crystal element 411 may be made of any material that can absorb radiation rays and emit a fraction of the absorbed radiation rays as light. For example, the crystal element 411 may be made of, for example, bismuth germanium oxide (BGO), lutetium oxyorthosilicate (LSO), lutetium-yttrium oxyorthosilicate (LYSO), lutetium-gadolinium oxyorthosilicate (LGSO), gadolinium oxyorthosilicate (GSO), yttrium oxyorthosilicate (YSO), barium fluoride, sodium iodide, cesium iodide, lead tungstate, yttrium aluminate, yttrium aluminate, lanthanum chloride, lutetium aluminum perovskite, lutetium disilicate, lutetium aluminate, lutetium iodide, thallium bromide, or the like, or any combination thereof. Different crystal elements 411 may be made of the same material or different materials.

The sizes and/or the shapes of different crystal elements 411 may be the same or different. For example, the crystal elements 411 of the crystal array 410 may have a uniform size and shape. As another example, different crystal elements 411 may have different lengths. As used herein, the length of a crystal element 411 may refer to its length along its extension direction, i.e., the third direction. In some embodiments, the size and/or the shape of a crystal element 411 may vary according to one or more conditions including, for example, an image resolution of the detector 400, a size of the detector 400, or the like, or any combination thereof.

In some embodiments, each of the plurality of photon-sensors 421 may be optically single-end-coupled with one or more crystal elements 411 of the crystal array 410. Different photon-sensors 421 may be coupled with the same number (or count) of or different numbers (or counts) of crystal elements 411. A photon-sensor 421 may be coupled to the corresponding crystal element(s) 411 in any suitable manner. For example, a photon-sensor 421 may contact the corresponding crystal element(s) 411 directly. As another example, a photon-sensor 421 may be fixed to the corresponding crystal element(s) 411 through one or more adhesive materials, e.g., a light transmitting glue. As still another example, a photon-sensor 421 may be single-end-coupled with the corresponding crystal element(s) 411 via a light transmitting material, e.g., a piece of glass. In some embodiments, one or more photon-sensors 421 may be optically coupled with a crystal element 411, e.g., any one of 411a-411d, to receive photons from a single end (e.g., the first end S1) of the crystal element 411. As used herein, a detector that uses one or more photon-sensors 421 to detect photons from a single end of each of the crystal elements 411 may be referred to as a detector having a single-end read-out structure.

In some embodiments, a photon-sensor 421 may include a phototube, a photomultiplier Tube (PMT), a photodiode, an active-pixel sensor, a bolometer, a gaseous ionization detector, a photoresistor, a phototransistor, an avalanche photodiode (APD), a single-photon avalanche photodiode (SPAD), a silicon photomultiplier (SiPM), a digital silicon photomultiplier (DSiPM), or the like, or any combination thereof. Different photon-sensors 421 may be of the same type or different types of photon-sensors.

In some embodiments, the crystal elements 411 of the crystal array 410 may form a plurality of crystal groups 430 along the first direction. Each crystal group 430 may include at least two crystal elements of the plurality of crystal elements 411. For example, as illustrated in FIG. 4, the crystal elements 411a and 411b may form a crystal group 430a, and the crystal elements 411c and 411d may form a crystal group 430b. It should be noted that the examples shown in FIG. 4 are merely provided for the purposes of illustration, and not intended to limit the scope of the present disclosure. A crystal group 430 may include any number or count of crystal elements 411. For example, the crystal elements 411a, 411b, 411c, and 411d may together form a crystal group 430.

In some embodiments, light sharing between two adjacent (or neighboring) crystal elements 411 belonging to one crystal group 430 may be allowed, while light sharing between two adjacent crystal groups may be restricted or substantially restricted, in order to facilitate the position determination of a photon gamma interaction. As used herein, two crystal elements 411 may be regarded as being adjacent to each other or neighboring if there is no other crystal element located between them. In some embodiments, two adjacent or neighboring crystal elements may be spaced apart by a void space, an item other than a crystal element (e.g., a film, a coating, a layer of a material different from the material of any crystal element of the neighboring crystal elements, etc.), or the like, or a combination thereof. Merely by way of example, a space may exist between two neighboring crystal elements, and a portion of the space may be filled with an optical separator (e.g., a second optical separator described elsewhere in the present disclosure) and a portion of the space may be void.

Two crystal groups may be regarded as being adjacent to or neighboring each other if there is no other crystal group located between them. In some embodiments, two adjacent or neighboring crystal groups may be spaced apart by a void space, an item other than a crystal element of a crystal group (e.g., a film, a coating, a layer of a material different from the material of any crystal element of the crystal elements of the neighboring crystal groups, etc.), or the like, or a combination thereof. Merely by way of example, a space may exist between two neighboring crystal groups, and a portion of the space may be filled with an optical separator (e.g., a first optical separator described elsewhere in the present disclosure) and a portion of the space may be void. As another example, a space between two neighboring crystal groups may be substantially completely filled with an optical separator (e.g., a first optical separator described elsewhere in the present disclosure).

To control the light transmission between two adjacent crystal elements 411 or crystal groups 430, a plurality of optical separators may be used in the detector 400. An optical separator may include a reflective film, a reflective foil, a reflective coating (e.g., a white reflective coating), or any other material that can prevent or substantially prevent light transmission. For example, as illustrated in FIG. 4, a first optical separator 412 of a first length may be configured between two adjacent crystal groups 430a and 430b. A second optical separator 413 of a second length may be configured between two adjacent crystal elements 411a and 411b of the crystal group 430a. The first length of the first optical separator 412 may be greater than the second length of the second optical separator 413, so that more space is available for optical photons to travel between the crystal groups 430a and 430b than between the crystal elements 411a and 411b. As used herein, a length of an optical separator may refer to its length along the extension direction of a crystal element 411, i.e., the third direction.

In some embodiments, the first optical separator 412 may extend along the third direction from the first end S1 of at least one of the two crystal elements 411 between which it is located, e.g., the crystal elements 411b and 411c. The length of the first optical separator 412 may be equal to or substantially equal to that of at least one of the crystal elements 411b and 411c, so as to completely or substantially completely block the light transmission between the crystal groups 430a and 430b.

In some embodiments, the second optical separator 413 may extend along the third direction from the first end S1 of at least one of the two crystal elements 411 between which it is located, e.g., the crystal elements 411a and 411b. The length of the second optical separator 413 may be less than that of at least one of the crystal elements 411a and 411b, so as to partially block the light transmission between the crystal elements 411a and 411b. In some embodiments, the length of the second optical separator 413 may be equal to or greater than a half of the length of at least one of the crystal elements 411a and 411b.

For illustration purposes, only one first optical separator 412 and one second optical separator 413 are illustrated in FIG. 4, but the detector 400 may include any number or count of first optical separators 412 and second optical separators 413. For example, the detector 400 may include a plurality of first optical separators 412 and/or a plurality of second optical separators 413. Each first optical separator 412 may be located between two adjacent or neighboring crystal groups 430, and extend along the third direction from the first end S1 of at least one of two adjacent crystal elements between which it is located. The length of each first optical separator 412 may be equal to a length of at least one of the two adjacent crystal elements between which it is located. Each second optical separator 413 may be located between two adjacent or neighboring crystal elements 411 of a crystal group 430, and extend along the third direction from the first end S1 of at least one of two adjacent or neighboring crystal elements between which it is located. The length of each second optical separator 413 may be less than a length of at least one of the two adjacent or neighboring crystal elements between which it is located. The lengths of different first optical separators 412 in the detector 400 may be the same or different. The lengths of different second optical separators 413 in the detector 400 may be the same or different. In some embodiments, the detector 400 may include a first optical separator 412 located between each pair of adjacent or neighboring crystal groups 430. Additionally or alternatively, the detector 400 may include a second optical separator 413 located between each pair of adjacent or neighboring crystal elements 411 of each crystal group 430.

It should be noted that the example illustrated in FIG. 4 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the crystal array 410 may include any suitable number or count of the crystal elements 411. For example, the crystal array 410 may include an even number or count (e.g., two, four, six, eight, or twelve) of the crystal elements 411. The crystal elements 411 may be arranged in any suitable manner. For example, the crystal elements 411 of the crystal array 410 may be arranged in a two-dimensional array including a plurality of rows and columns. In some embodiments, the first length of a first optical separator 412 may be equal to the second length of a second optical separator 413

Figure 5:
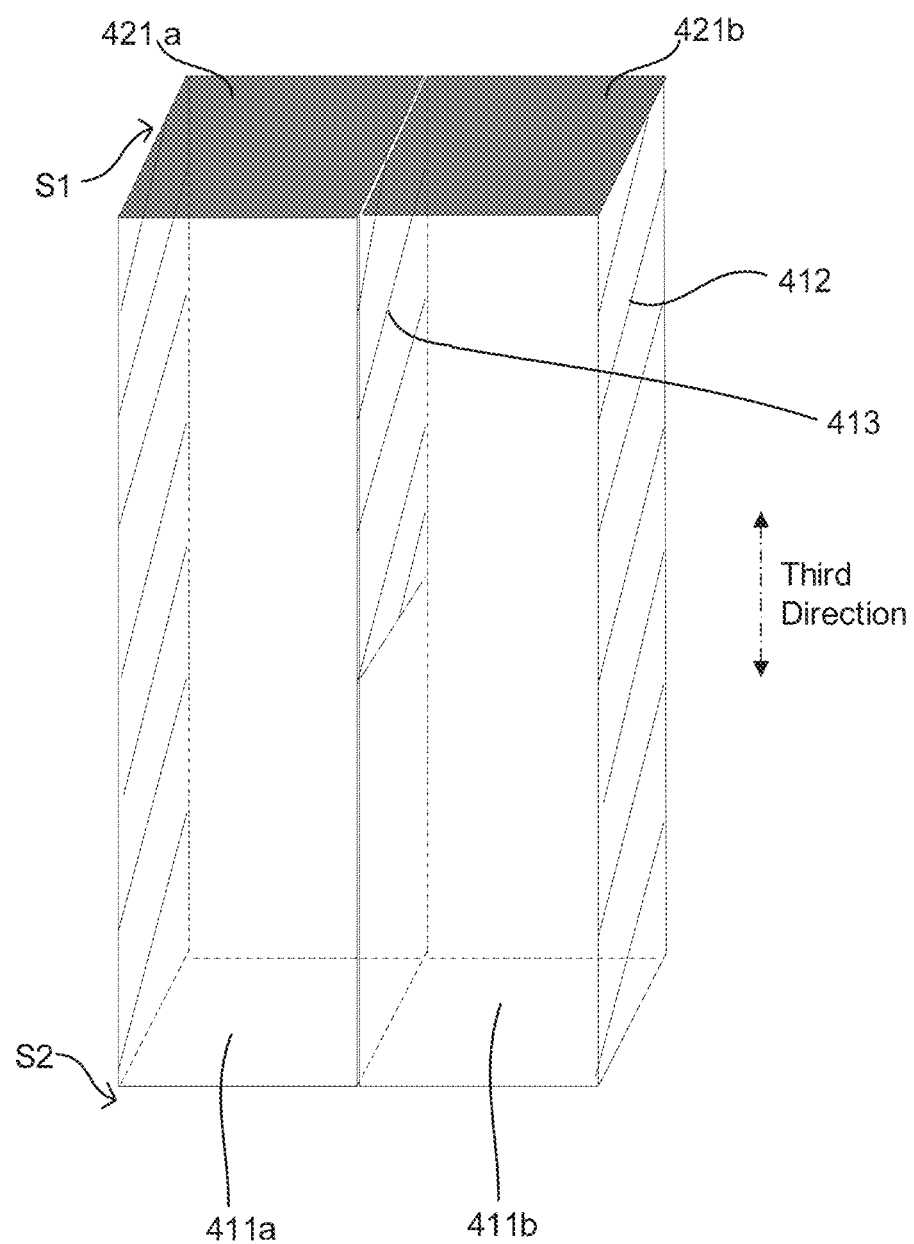
FIG. 5 is a schematic diagram illustrating a perspective view of an exemplary crystal group according to some embodiments of the present disclosure.

FIG. 5 is a schematic diagram illustrating a perspective view of an exemplary crystal group 430a according to some embodiments of the present disclosure. As described in connection with FIG. 4, the crystal group 430a may include the crystal element 411a and the crystal element 411b. The photon-sensor 421a and the photon-sensor 421b (shown as darkened areas in FIG. 5) may be optically coupled with the crystal element 411a and the crystal element 411b, respectively.

The shaded areas illustrated in FIG. 5 represent one or more optical separators configured to block or partially block the light transmission between the crystal elements 411. For example, the first optical separator 412 may substantially or completely cover a side surface of the crystal element 411b to prevent the optical photons in the crystal group 430a from travelling through the side surface facing an adjacent crystal group to the adjacent crystal group (not shown in FIG. 5). The first length of the first optical separator 412 may be equal to the length of the crystal element 411b. The second optical separator 413 may be located between the crystal elements 411a and 411b. The second optical separator 413 may extend along the third direction from the first end S1 of crystal element 411a or 411b. The second length of the second optical separator 413 may be less than the length of the crystal element 411a or 411b so that it may partially block the optical photon transmission between the crystal elements 411a and 411b.

In some embodiments, the length of the second optical separator 413 may be equal to N % of the length of the crystal element 411a or 411b. N may have any suitable positive value. In some embodiments, N may be in the range of 30 to 90, 50 to 85, etc. For example, N may be 30, 40, 50, 60, 70, 80, 85, or 90. N may be a parameter used in the position determination of a photon gamma interaction in the detector 400. In some embodiments, N may be a default parameter stored in a storage device (e.g., the storage device 150). Additionally or alternatively, N may be set manually or be determined by one or more components of the imaging system 100 according to different situations.

Figure 6A:
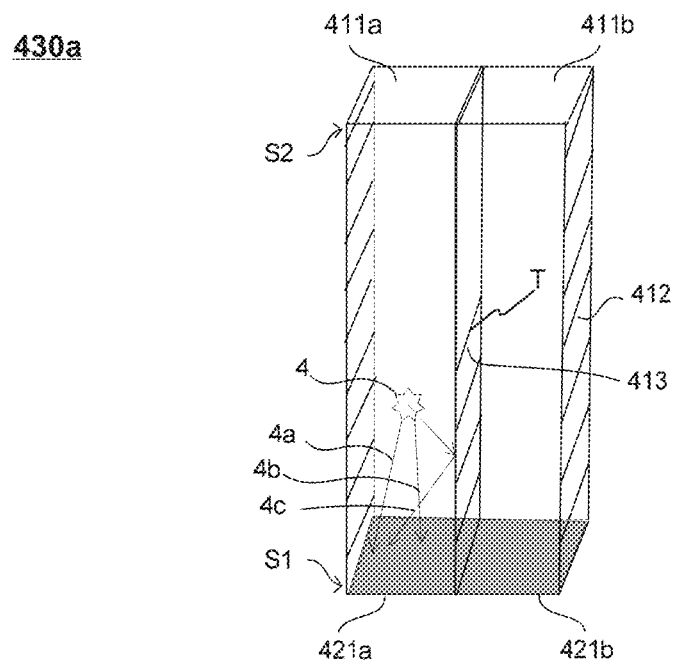
FIG. 6a is a schematic diagram illustrating exemplary photon gamma interactions occurred in an exemplary crystal group according to some embodiments of the present disclosure.
Figure 6B:
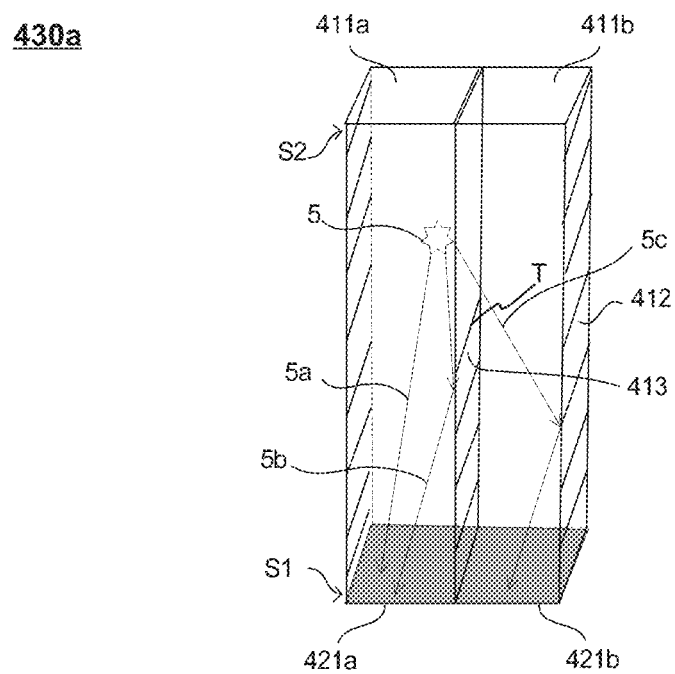
FIG. 6b is a schematic diagram illustrating exemplary photon gamma interactions occurred in an exemplary crystal group according to some embodiments of the present disclosure.

FIGS. 6a and 6b are schematic diagrams illustrating exemplary photon gamma interactions occurred in an exemplary crystal group 430a according to some embodiments of the present disclosure.

A photon gamma interaction occurred in the crystal group 430a may excite one or more optical photons that may be detected by the corresponding photon-sensors 421a and/or 421b as described elsewhere in this disclosure. The number or count of optical photons detected by the photon-sensor 421a or 421b may be associated with a position of the photon gamma interaction in the crystal group 430a. For example, as illustrated in FIG. 6a, a photon gamma interaction 4 occurs at a position closer to the first end S1 (or lower) than the top of the second optical separator 413 (denoted as T in FIG. 6a). The optical photon(s) produced by the photon gamma interaction 4 may be blocked or substantially blocked by the second optical separator 413 from travelling into the crystal element 411b. Accordingly, all or almost all the optical photons excited by the photon gamma interaction 4 may be detected by the photon-sensor 421a. Merely by way of example, as shown in FIG. 6a, the photon gamma interaction 4 may generate three optical photons 4a, 4b, and 4c. The optical photons 4a and 4b are detected by the photon-sensor 421a directly, and the optical photon 4c is reflected by the second optical separator 413 and then detected by the photon-sensor 421a.

As another example, as illustrated in FIG. 6b, a photon gamma interaction 5 occurs at a position farther to the first end S1 (or higher) than the top of the second optical separator 413 (denoted as T in FIG. 6b). The optical photon(s) excited by the photon gamma interaction 5 may be partially blocked by the second optical separator 413 from travelling into the crystal element 411b. Accordingly, the optical photons may be detected by both the photon-sensor 421a and the photon-sensor 421b. Merely by way of example, the photon gamma interaction 5 may generate three optical photons 5a, 5b, and 5c. The optical photons 5a and 5b are detected by the photon-sensor 421a directly, and the optical photon 5c travels into the crystal element 411b and is detected by the photon-sensor 421b.

Figure 7:
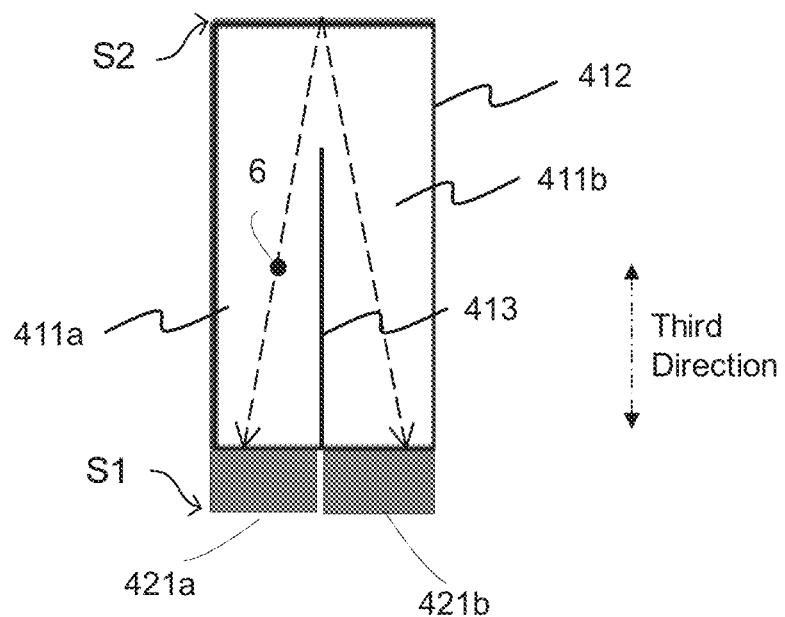
FIG. 7 is a schematic diagram illustrating an exemplary crystal group according to some embodiments of the present disclosure.

FIG. 7 is a schematic diagram illustrating an exemplary crystal group 700 according to some embodiments of the present disclosure.

The crystal group 700 may be similar to the crystal group 430a as described in connection with FIGS. 4 to 6, except that the second ends S2 of the crystal elements 411a and 411b may be integrated into a single end. In some embodiments, the crystal group 700 may be manufactured by partially cutting a single crystal block into the crystal elements 411a and 411b. The cut may be extended from the first end S1 of the crystal block toward its second end S2, and the cut may extend to a depth without reaching the second end S2. The second optical separator 413 may be made by filling the cutting grooves of the crystal block with one or more light reflecting materials. In such a case, the light transmission between the crystal elements 421a and 421b may be allowed in the uncut portion near the second end S2 while be prevented in the cut portion near the first end S1. The first optical separator(s) 412 may be formed by coating a side surface of the crystal elements 411a and/or 411b with a light reflecting material. In such a case, the light transmission between the crystal group 700 and an adjacent group (not shown in FIG. 7) may be prevented.

In some embodiments, the position of a photon gamma interaction 7 in the crystal group 700 may be determined based on the output information of the photon-sensors 421a and 421b. The output information may reflect the energy of the optical photons excited by the photon gamma interaction 6 and detected by the photon-sensors 421a and/or 421b. In some embodiments, the crystal element in which the photon gamma interaction 6 occurs (also referred to as a target crystal element), and/or the depth of the photon gamma interaction 6 in the target crystal element may be determined based on the output information. More descriptions regarding the determination of a position of a photon gamma interaction may be found elsewhere in the present disclosure. See, e.g., FIGS. 16 and 17 and relevant descriptions thereof.

Figure 8A:
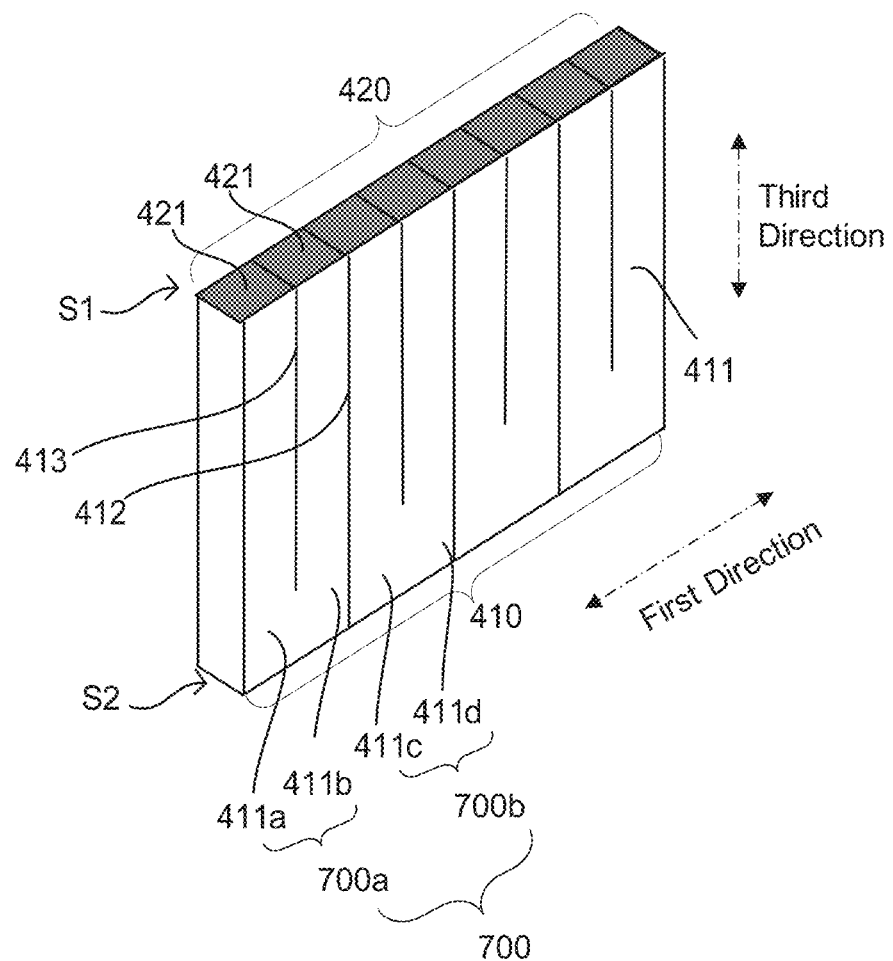
FIG. 8a is a schematic diagram illustrating an exemplary detector according to some embodiments of the present disclosure.

FIG. 8a is a schematic diagram illustrating an exemplary detector 800a according to some embodiments of the present disclosure. In some embodiments, the detector 800a may be an example of the detector 112 or a portion of the detector 112. The detector 800a may be similar to the detector 400, except for certain components or features.

As illustrated in FIG. 8a, the detector 800a may include a plurality of crystal groups 700 (e.g., a crystal group 700a and a crystal group 700b) arranged along the first direction. The second ends S2 of the crystal elements 411 in each crystal group 700 may be integrated into a single end. For example, the second ends S2 of the crystal elements 411a and 411b of the crystal group 700a may form an integrated end.

In some embodiments, the detector 800a may be made by cutting a single crystal block along the third direction to generate a plurality of cuts. The cuts may extend from the first end S1 of the crystal block and have various lengths along the third direction. For example, to form the plurality of crystal groups 700, one or more first cuts may be made to penetrate the crystal block from its first end S1 to its second end S2. The cutting grooves of the first cuts may be filled at least partially with one or more light reflecting materials, and the light reflecting material(s) in each cutting groove may form a first optical separator 412. As another example, to form the crystal elements in each crystal group 700, one or more second cuts may be made from the first end S1 toward but not reaching the second end S2. The cutting grooves of the second cuts may be filled at least partially with one or more light reflecting materials, and the light reflecting material(s) in each cutting groove may form a second optical separator 413.

In some embodiments, the detector 800a may be manufactured by assembling a plurality of crystal groups 700 along the first direction. Each crystal group 700 may be manufactured in a similar manner as described in FIG. 7. The crystal groups 700 may be assembled together in any suitable manner, for example, by one or more adhesive materials.

Figure 8B:
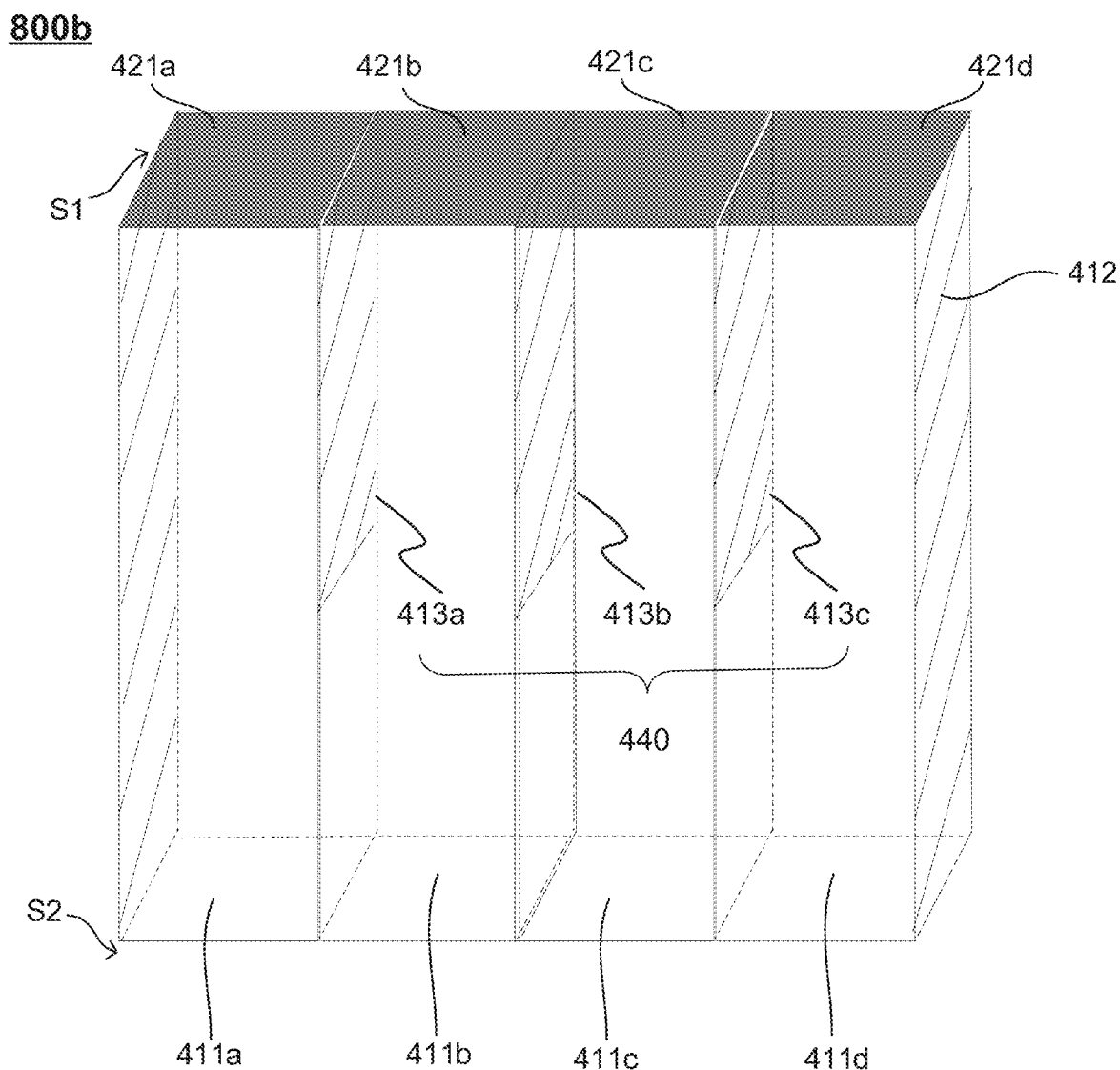
FIG. 8b is a schematic diagram illustrating a perspective view of an exemplary crystal group according to some embodiments of the present disclosure.

FIG. 8b is a schematic diagram illustrating a perspective view of an exemplary crystal group 800b according to some embodiments of the present disclosure. The crystal group 800b may be similar to the crystal group 430 (e.g., the crystal group 430a) as described elsewhere in this disclosure (e.g., FIGS. 4 and 5 and relevant descriptions), except for certain components or features.

The crystal group 800b may include the crystal elements 411a, 411b, 411c, and 411d. The photon-sensors 421a, 421b, 421c, and 421d may be optically coupled with the crystal elements 411a, 411b, 411c, and 411d, respectively. A first optical separator 412 may substantially or completely cover a side surface of the crystal group 800b to prevent optical photons from travelling through the side surface facing an adjacent crystal group to the adjacent crystal group (not shown in FIG. 8b). A second optical separator 413 (e.g., 413a, 413b, and 413c) may be positioned between each pair of adjacent crystal elements in the crystal group 800b. The length of each second optical separator 413 in the second optical separator group 440 may be smaller than the length of the first optical separator 412. The lengths of different second optical separators 413 may be the same or different. In some embodiments, the second optical separators 413a, 413b, and 413c may form a second optical separator group 440.

It should be noted that the examples illustrated in FIGS. 7 to 9 are merely provided for the purposes of illustration, and not intended to limit the scope of the present disclosure. A crystal group (e.g., the crystal group 700 or 800b) may include any number or count of crystal elements 411. The second ends S2 of crystal elements 411 in a crystal group may be separate or integrated into a single end.

Figure 9A:
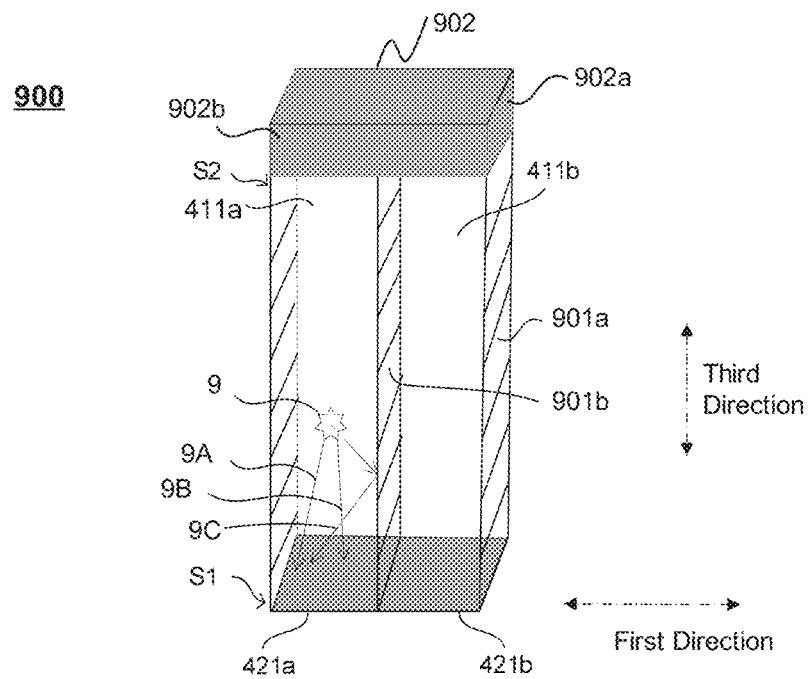
FIG. 9a is a schematic diagram illustrating exemplary photon gamma interactions occurred in an exemplary crystal group according to some embodiments of the present disclosure.
Figure 9B:
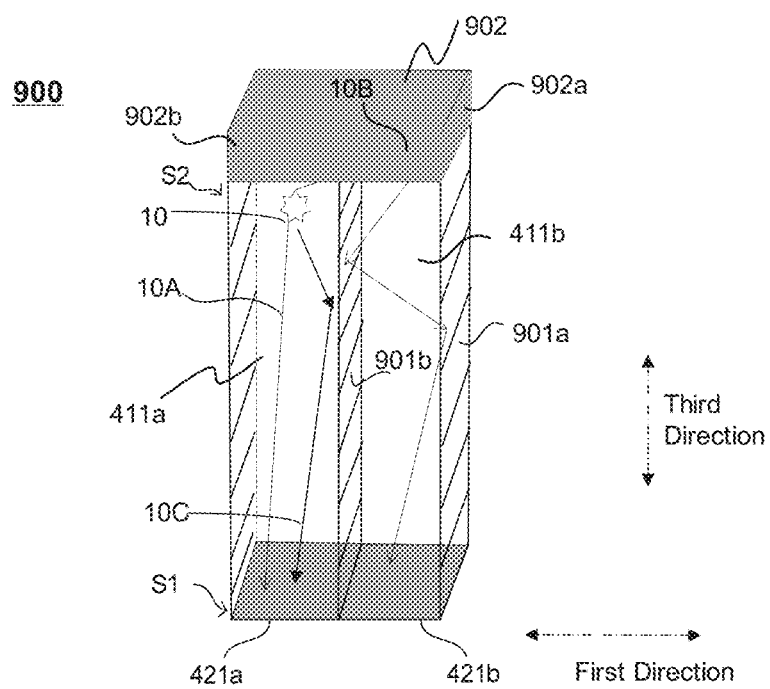
FIG. 9b is a schematic diagram illustrating exemplary photon gamma interactions occurred in an exemplary crystal group according to some embodiments of the present disclosure.

FIGS. 9a and 9b are schematic diagrams illustrating exemplary photon gamma interactions occurred in an exemplary crystal group 900 according to some embodiments of the present disclosure. The crystal group 900 may be similar to the crystal group 430a as described in connection with FIGS. 4 to 6 except for certain features including those described below.

As shown in FIGS. 9a and 9b, the crystal group 900 may include a crystal element 411a, a crystal element 411b, and an optical window (not shown in figures). The optical window may allow light transmission between the two crystal elements 411a and 411b of the crystal group 900 so that a photon excited by an photon gamma interaction in a first crystal element of the crystal group 900 can travel into a second crystal element of the crystal group 900 through the second end of the first crystal element, the optical window, and the second end of the second crystal element. For example, a photon excited by a photon gamma interaction in the crystal element 411a may travel into the crystal element 411b through the second end S2 of the crystal element 411a, the optical window, and the second end S2 of the crystal element 411b.

In some embodiments, the optical window may include a plurality of optical separators and a light transmission medium 902. For each of crystal elements of the crystal group 900, an optical separator may be mounted on each side surface of the crystal element facing a neighboring crystal element of the crystal element along the first direction. The optical separator may be similar to the first optical separator 412 as described elsewhere in this disclosure. See, e.g., FIGS. 4 to 8b and the relevant descriptions. The length of the optical separator may be equal to or substantially equal to a length of at least one of the crystal element or the neighboring crystal element. For example, as illustrated in FIGS. 9a and 9b, an optical separator 901a may be mounted on a right side surface of the crystal element 411b facing a neighboring crystal element in a neighboring crystal group (not shown in figures) along the first direction. The length of the optical separators 901a may be equal to the crystal element 411b to prevent a photon in the crystal element 411b from travelling through the right side surface of the crystal element 411 to a neighboring crystal element (not shown in figures). An optical separator 901b may be mounted between a right side surface of the crystal element 411a and a left side surface of the crystal element 411b along the first direction as illustrated in FIGS. 9a and 9b. The length of the optical separators 901b may be equal to the crystal element 411b and/or the crystal element 411a to prevent a light transmission between the crystal elements 411a and 411b through their side surfaces facing each other.

In some embodiments, two neighboring crystal elements of the crystal group 900 may share an optical separator (e.g., a reflective film) located between the two neighboring crystal elements. Alternatively, each of the two neighboring crystal elements may be coated with an optical separator on its side surface facing the other crystal element of the crystal group 900. For example, both the right side surface of the crystal element 411a and the left side surface of the crystal element 411b may be coated with a reflective coating.

The light transmission medium 902 may cover the second ends S2 of the crystal elements 411a and 411b. Each side surface of the light transmission medium 902 that faces the light transmission medium 902 of a neighboring crystal group of the crystal group 900, e.g., side surfaces 902a and 902b may be coated with a light reflective material so as to completely or substantially completely prevent a photon in the crystal group 900 from traveling out of the light transmission medium 902 from the side surfaces of the light transmission medium 902. The light transmission medium 902 may be made of any material substance (e.g., glass) that allows light to pass through. Photons excited by a photon gamma interaction occurred in one crystal element of the crystal group 900 may travel into the light transmission medium 902, be reflected by one of the side surfaces of the light transmission medium 902 for one or more times, and then travel into another crystal element of the crystal group 900. For example, as illustrated in FIG. 9b, a photon 10B generated by photon gamma interaction 10 in the crystal element 411a may travel into the crystal element 411b through the light transmission medium 902.

The position of a photon gamma interaction occurred in the crystal group 900 may be determined based on the output information of the photon-sensors 421a and 421b optically coupled with the crystal group 900. In some embodiments, the position of a photon gamma interaction may be determined based on the energy detected by the photon-sensors 421a and 421b. For example, as illustrated in FIG. 9a, a photon gamma interaction 9 occurs at a position closer to the first end S1 than the second end of the crystal element 411a. All or most all the photons (e.g., photon 9A, 9B, and 9C) produced by the photon gamma interaction 9 may be detected by the photon-sensor 421b optically coupled with the crystal element 411a. As another example, as illustrated in FIG. 9b, the photon gamma interaction 10 occurs at a position closer to the second end S2 than the first end S1 of the crystal element 411a. A portion of the photons generated by the photon gamma interaction 10 (e.g., photons 10A and 10B) may be detected by the photon-sensor 421a. A portion of the photons (e.g., the photon 10B) may travel into the crystal element 411b via the light transmission medium 902, and be detected by the photon-sensor 421b. In some embodiments, the photon gamma interaction position may be determined by performing process 1600 as described in connection with FIG. 16.

Additionally or alternatively, the position of a photon gamma interaction in the crystal group 900 may be determined based on the time when the photons generated by the photon gamma interaction are received the photon-sensors 421a and 421b. Taking the photon gamma interaction 10 as an example, a time difference between a first time point when the photon-sensor 421a receives a photon (e.g., the photon 10A) and a second time point when the photon-sensor 421b receives a photon (e.g., the photon 10B) may be determined. The DOI of the photon gamma interaction 10 may be estimated based on the time difference and the speed of light. A shorter time difference may indicate that the photon gamma interaction 10 is occurred at a position closer to the second end of the crystal element 411a.

It should be noted that the crystal group 900 shown in FIGS. 9a and 9b are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the light transmission medium 902 may have any shape and size. In some embodiments, the crystal group 900 may include any number or count of crystal elements.

Figure 10A:
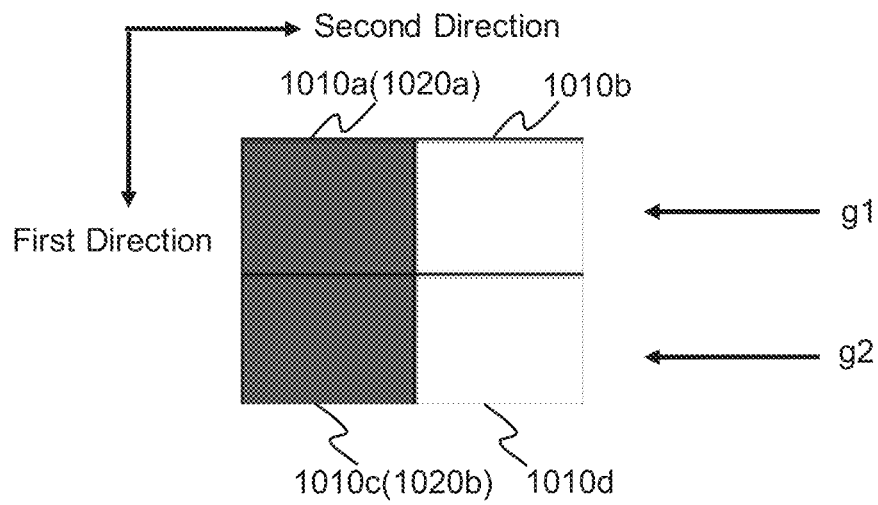
FIG. 10a is a schematic diagram illustrating a top view of an exemplary detector according to some embodiments of the present disclosure.
Figure 10B:
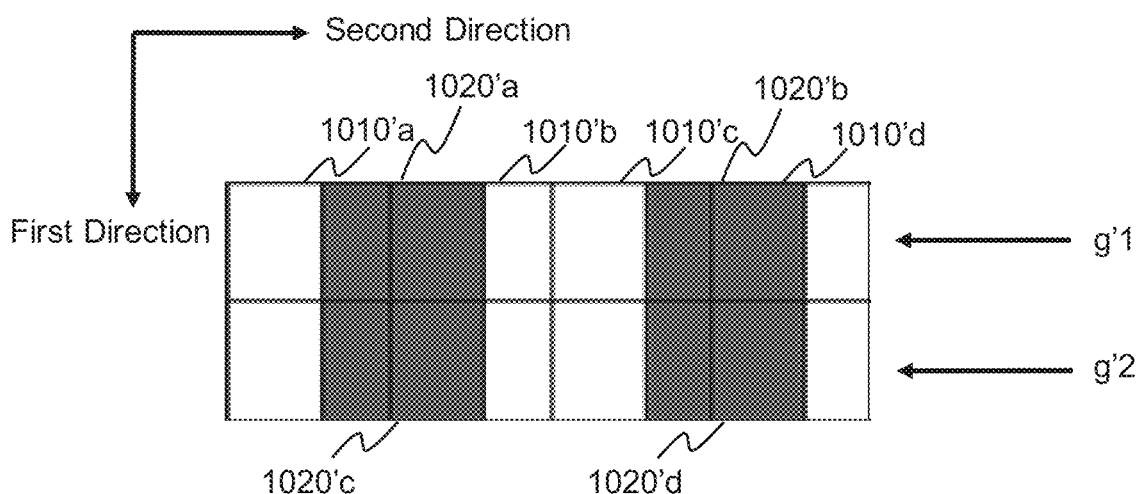
FIG. 10b is a schematic diagram illustrating a top view of an exemplary detector according to some embodiments of the present disclosure.

FIGS. 10a and 10b are schematic diagrams respectively illustrating top views of an exemplary detector 1000a and an exemplary detector 1000b according to some embodiments of the present disclosure.

The detectors 1000a may include a crystal array and a photon-sensor array (shown as darkened areas in FIG. 10a) optically coupled with the crystal array. The crystal array may include a plurality of crystal elements arranged along a first direction and a second direction. Along the first direction, the crystal elements may form a plurality of columns of crystal elements and define one or more crystal groups. Along the second direction, the crystal elements may form a plurality of rows. In some embodiments, the second direction may be orthogonal to or approximately orthogonal to the first direction. In some embodiments, the first direction may be along the Z-axis, and the second direction may be along the X-axis of a PET imaging device 110 as illustrated in FIG. 1.

As illustrated in FIG. 10a, the detector 1000a may include two crystal element rows (i.e., a first crystal row g1 and a second crystal row g2) and two crystal columns. The first crystal row g1 may include two crystal elements 1010a and 1010b arranged side by side along the second direction, and the second crystal row g2 may include two crystal elements 1010c and 1010d arranged side by side along the second direction.

The photon-sensor array may include a plurality of photon-sensors configured to receive optical photons emitted from the crystal elements of the detector 1000a. Each photon-sensor may be optically coupled with one or more crystal elements. For example, as illustrated in FIG. 10a, the photon-sensor array may include a photon-sensor 1020a and a photon-sensor 1020b. The photon-sensor 1020a may directly or indirectly contact an end of the crystal element 1010a, optically coupled with at least one of the crystal elements 1010a and 1010b (e.g., optically coupled with the crystal element 1010a) and configured to receive optical photons emitted from the crystal elements 1010a and 1010b. The photon-sensor 1020b may directly or indirectly contact an end of the crystal element 1010c, optically coupled with the crystal element 1010c and configured to receive optical photons emitted from the crystal elements 1010c and 1010d.

The detector 1000b may be similar to the 1000a, except for certain components or features. The detector 1000b may include a first crystal row g'1 and a second crystal row g'2, each of which may include four crystal elements. The photon-sensor array may include photon-sensors 1020'a, 1020'b, 1020'c, and 1020'd. Each photon-sensor may be optically coupled with two crystal elements that belong to one crystal row. For example, the photon-sensor 1020'a may be coupled with crystal elements 1010'a and 1010'b in the first crystal row g'1 and configured to detect optical photons emitted from them. In some embodiments, the photon-sensor 1020'a and the photon-sensor 1020'b may be aligned with the photon-sensor 1020'c and the photon-sensor 1020'd along the first direction, respectively.

In some embodiments, the crystal elements in a crystal column may form one or more crystal groups (not shown in FIGS. 10a and 10b) along the first direction. Each crystal group may include at least two crystal elements. One or more optical separators, arranged between crystal elements and/or crystal groups, may be used in the detector 1000a and/or the detector 1000b to control light transmission. More descriptions of the optical separators (e.g., a first, a second, and a third optical separator) may be found elsewhere in the present disclosure (e.g., FIG. 11 and the descriptions thereof).

It should be noted that the detectors 1000a and 1000b shown in FIGS. 10a and 10b are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the detector 1000a and/or 1000b may include any number or count of rows and columns of crystal elements. A photon-sensor may be optically coupled with any number or count of crystal elements. For example, the photon-sensor 1020a may be optically coupled with the crystal elements 1010*a*, 1010*b*, 1010*c*, and 1010*d*, and configured to detect optical photons emitted from the crystal elements 1010*a*, 1010*b*, 1010*c*, and 1010*d*. Different photon-sensors may be optically coupled with the same number or count of or different numbers or counts of crystal elements.

Figure 11A:
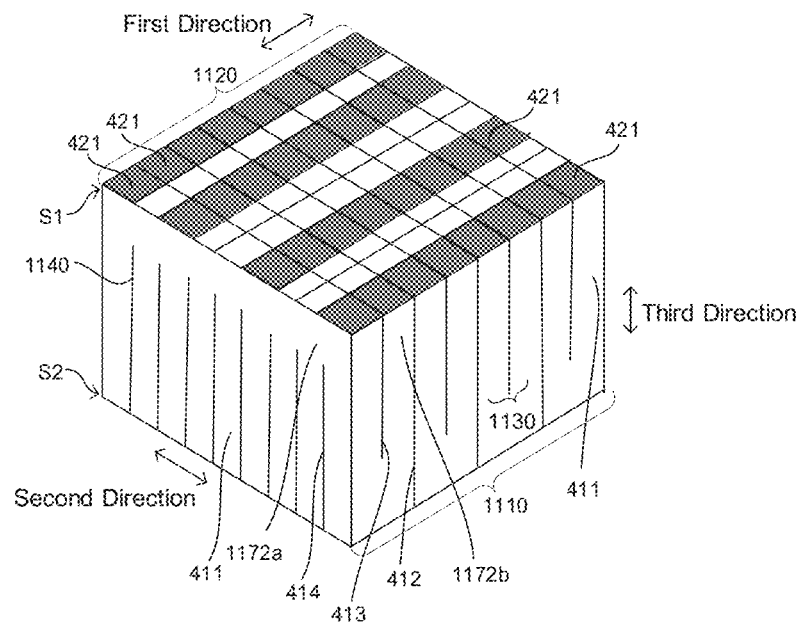
FIG. 11a is a schematic diagram illustrating an exemplary detector according to some embodiments of the present disclosure.

FIG. 11*a* is a schematic diagram illustrating an exemplary detector 1100*a* according to some embodiments of the present disclosure. In some embodiments, the detector 1100*a* may be an example of the detector 112 or a part of the detector 112.

The detector 1100*a* may include a crystal array 1110 and a photon-sensor array 1120 optically coupled with the crystal array 1110. The crystal array 1110 may be similar to the crystal array 410 as described in connection with FIG. 4, except for certain components or features. The crystal elements 411 of the crystal array 1110 may form a plurality of crystal rows arranged in the second direction and a plurality of crystal columns arranged in the first direction. For example, as shown in FIG. 11*a*, the crystal array 1110 may have a configuration of 9×8 crystal elements. In some embodiments, the second direction may be orthogonal or approximately orthogonal to the first direction. In some embodiments, both of the first direction and the second direction may be orthogonal or approximately orthogonal to an extension direction of the crystal elements of the crystal array 1110 (i.e., the third direction). In some embodiments, the first direction, the second direction, and the third direction may be along the Z-axis, the X-axis, and the Y-axis, respectively, of a PET imaging device 110 as illustrated in FIG. 1.

The photon-sensor array 1120 may include a plurality of photon-sensors 421 arranged along the first direction and the second direction. Each photon-sensor 421 may be optically coupled with one or more of the crystal elements of the crystal array 1110. For example, along the first direction, each photon-sensor 421 may be optically coupled with one crystal element 411 of a crystal column. Along the second direction, each photon-sensor 421 may be optically coupled with one or more crystal elements 411 of a crystal row. In some embodiments, a photon-sensor 421 may completely cover the first ends S1 of two adjacent crystal elements 411, and configured to receive optical photons emitted from the two adjacent crystal elements 411. Alternatively, a photon-sensor 421 may completely cover a first end of a crystal element 411, and configured to detect optical photons emitted from the crystal element 411 and an adjacent or neighboring crystal element of the crystal element 411. A photon-sensor 421 may be optically coupled with the corresponding crystal element(s) 411 in any suitable manner as described elsewhere in the present disclosure (e.g., FIG. 4 and the descriptions thereof).

In some embodiments, in each crystal column, the corresponding crystal elements 411 may form a plurality of crystal groups 1130 along the first direction. The crystal groups 1130 may be similar to the crystal group 700 in FIG. 7. The light transmission between and within the crystal groups 1130 may be controlled by applying one or more first optical separators 412 and one or more second optical separators 413. The arrangement of the first optical separator(s) 412 and second optical separator(s) 413 in and within a crystal group 1130 may be similar to that of the crystal group 700, and the descriptions thereof are not repeated.

Additionally or alternatively, in a crystal row, the light transmission between two adjacent crystal elements 411 along the second direction may be controlled by applying a plurality of third optical separators 1140. For example, as illustrated in FIG. 11*a*, each third optical separator 1140 may be located between two adjacent crystal elements 411 along the second direction. Each third optical separator 1140 may extend along the third direction from the second end S2 of at least one of the two crystal elements 411 between which it is located. The length of each third optical separator 1140 may be equal to or less than a length of at least one of the crystal elements between which it is located. The lengths of different third optical separators 1140 may be the same or different. In some embodiments, the length of a third optical separator 1140 may be equal to the length of at least one of the crystal elements between which it is located.

In some embodiments, the third optical separators 1140 may be of the same length when a ratio of the number of the crystal elements 411 to the number of the photon-sensors 421 in the detector 1100*a* is lower than a threshold (such as 2, 3, 5, 10). In some embodiments, a third optical separator 1140 may be of a greater length if it is located closer to the edge of the crystal array 1110. In some embodiments, a plurality of third optical separators 1140 in a crystal row may form a third optical separator group. In some embodiments, the plurality of third optical separators 1140 may be periodically arranged in the third optical separator group. Descriptions regarding the arrangement of the third optical separators may be found in, for example, CN Application No. 201410231483.6 filed on May 28, 2014, which is hereby incorporated by reference.

Figure 11B:
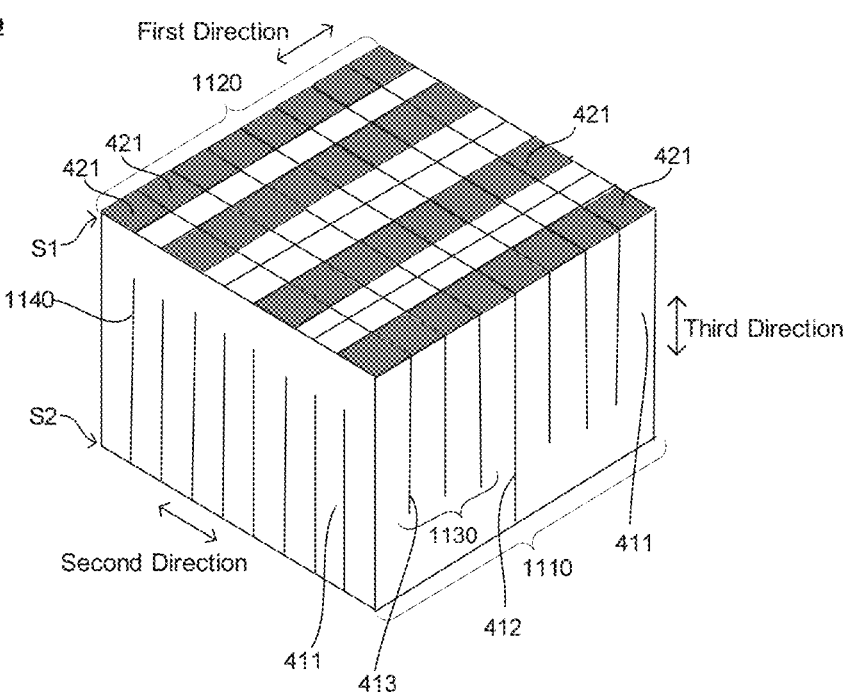
FIG. 11b is a schematic diagram illustrating an exemplary detector according to some embodiments of the present disclosure.

FIG. 11*b* is a schematic diagram illustrating an exemplary detector 1100*b* according to some embodiments of the present disclosure. The detector 1100*b* may be similar to the detector 1100*a*, except for certain components or features. For example, each crystal group in each crystal column of the detector 1100*b* may include four crystal elements 411.

It should be noted that the detectors 1100*a* and 1100*b* are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the crystal array 1110 may include any number or count of crystal rows and any number or count of crystal columns. The number or count of the crystal rows and the number or count of the crystal columns may be the same or different. In some embodiments, the second ends S2 of the crystal elements 411 of a crystal group 1130 may be integrated into a single end. In some embodiments, a third optical separator 1140 may be replaced by an external light guide (e.g., a piece of glass) when the ratio of the number or count of the crystal elements 411 to the number or count of the photon-sensors 421 in the detector 1100*a* or 1100*b* is lower than a threshold (such as 2, 3, 5, 10).

Figure 12A:
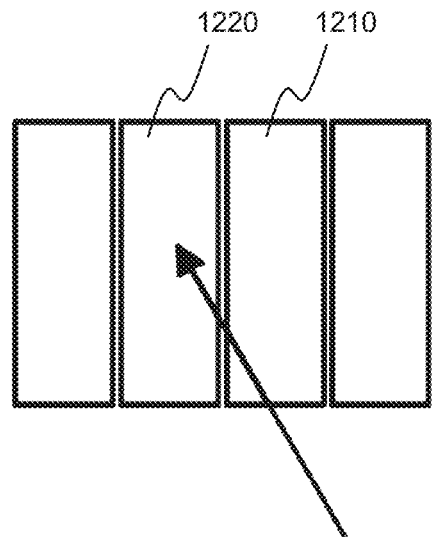
FIG. 12a is a schematic diagram illustrating an exemplary inter-crystal penetration phenomenon according to some embodiments of the present disclosure.
Figure 12B:
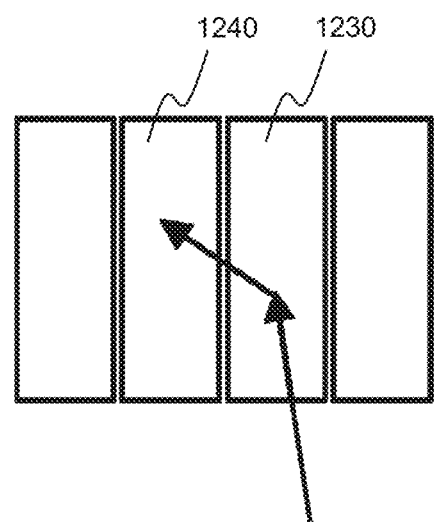
FIG. 12b is a schematic diagram illustrating an exemplary inter-crystal scatter (ICS) phenomenon according to some embodiments of the present disclosure.

FIG. 12*a* is a schematic diagram illustrating an exemplary inter-crystal penetration phenomenon according to some embodiments of the present disclosure. FIG. 12*b* is a schematic diagram illustrating an exemplary inter-crystal scatter (ICS) phenomenon according to some embodiments of the present disclosure.

When an annihilation photon travels through crystal elements of a PET device, it may undergo an ICS and/or an inter-crystal penetration phenomenon, which may result in a reduction in the resolution of the PET device. As shown in FIG. 12*a*, the inter-crystal penetration phenomenon occurs when an annihilation photon passes through a crystal element 1210 without interacting with the crystal element 1210, interacts with another crystal element 1220, and a corresponding optical photon is detected by a photon-sensor corresponding to the crystal element 1220. In some embodiments, the inter-crystal penetration may be more likely to occur to an annihilation photon that enters a crystal element from an angle (with the vertical direction along the length of the crystal element in the extension direction), for an annihilation photon of a higher energy, and/or when the attenuation coefficient of the detector material decreases.

As shown in FIG. 12b, an ICS occurs when an annihilation photon enters a crystal element 1230, undergoes one or more Compton scatters, interacts with one or more crystal elements other than the crystal element 1230, and a corresponding optical photon is detected by one or more photon-sensors corresponding the crystal element(s) other than the crystal element 1230, such as a crystal element 1240. In some embodiments, ICS may be likely to occur to annihilation photons that enter the crystal elements vertically (e.g., along the length of the crystal element 1230 in its extension direction) or non-vertically.

Both the ICS phenomenon and inter-crystal penetration phenomenon may cause an inaccurate DOI determination and LOR assignment because an annihilation photon may excite an optical photon that is detected by a photon-sensor optically coupled with a crystal element other than the one from which the annihilation photon initially enters. As such, the ICS phenomenon and/or inter-crystal penetration phenomenon may need to be considered in the DOI determination.

Figure 13:
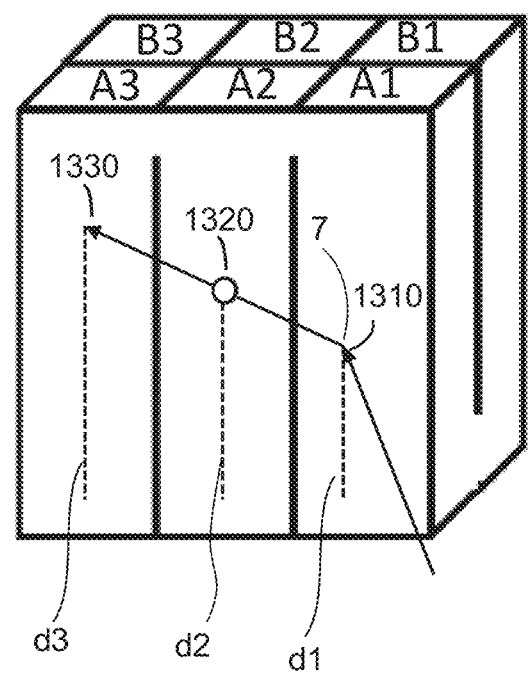
FIG. 13 is a schematic diagram illustrating an exemplary ICS phenomenon in an exemplary crystal array according to some embodiments of the present disclosure.

FIG. 13 is a schematic diagram illustrating an exemplary ICS phenomenon in an exemplary crystal array 1300 according to some embodiments of the present disclosure. As illustrated, the crystal array 1300 may include a plurality of crystal elements A1, A2, A3, B1, B2, and B3. The crystal elements A1 and B1 may form a crystal group A1/B1, the crystal elements A2 and B2 may form a crystal group A2/B2, and the crystal elements A3 and B3 may form a crystal group A3/B3. A plurality of photon-sensors (not shown in FIG. 13) may be optically coupled with one or more of the crystal elements of the crystal array 1300 to detect optical photons emitted from the corresponding crystal element(s). For illustration purposes, the photon-sensors optically coupled with the crystal elements in one crystal group may be referred to as a photon-sensor group.

In some embodiments, an annihilation photon may undergo an ICS when travelling in a crystal element from which it initially enters. For example, as shown in FIG. 13, an annihilation photon may be scattered after entering the crystal element A1, and the optical photon(s) produced by the annihilation photon may be detected in one or more of the crystal groups A1/B1, A2/B2, and A3/B3. In some embodiments, the annihilation photon may interact with the crystal element A1 (shown as a photon gamma interaction 7 in FIG. 13). The position of the photon gamma interaction 7 may be determined based on the respective energy detected in the crystal groups A1/B1, A2/B2, and A3/B3. Without considering the ICS, the position of the photon gamma interaction 7 may be determined inaccurately. For example, a position 1320 may be determined as the position of the photon gamma interaction 7 if the ICS is neglected.

Methods for determining the position of a photon gamma interaction (e.g., the photon gamma interaction 7) provided herein may take the ICS phenomenon into consideration. For example, in each crystal group, a candidate position may be determined based on the energy detected by the corresponding photon-sensor group. Each candidate position in a crystal group may include a candidate depth of the photon gamma interaction within the crystal group. Then the position of the photon gamma interaction may be determined based on the candidate positions. In some embodiments, the candidate position with the smallest candidate depth may be selected as the position of the photon gamma interaction. For example, as illustrated in FIG. 13, a candidate position 1310 with a candidate depth d1, a candidate position 1320 with a candidate depth d2, and a candidate position 1330 with a candidate depth d3 may be determined in the crystal groups A1/B1, A2/B2, and A3/B3, respectively. The candidate position 1310 has the smallest candidate depth, showing that it is the initial position of the photon gamma interaction 7 and therefore is deemed as the position of the photon gamma interaction 7. More descriptions regarding the determination of a photon gamma interaction may be found elsewhere in the present disclosure. See, e.g., FIGS. 16 and 17 and relevant descriptions thereof.

Figure 14A:
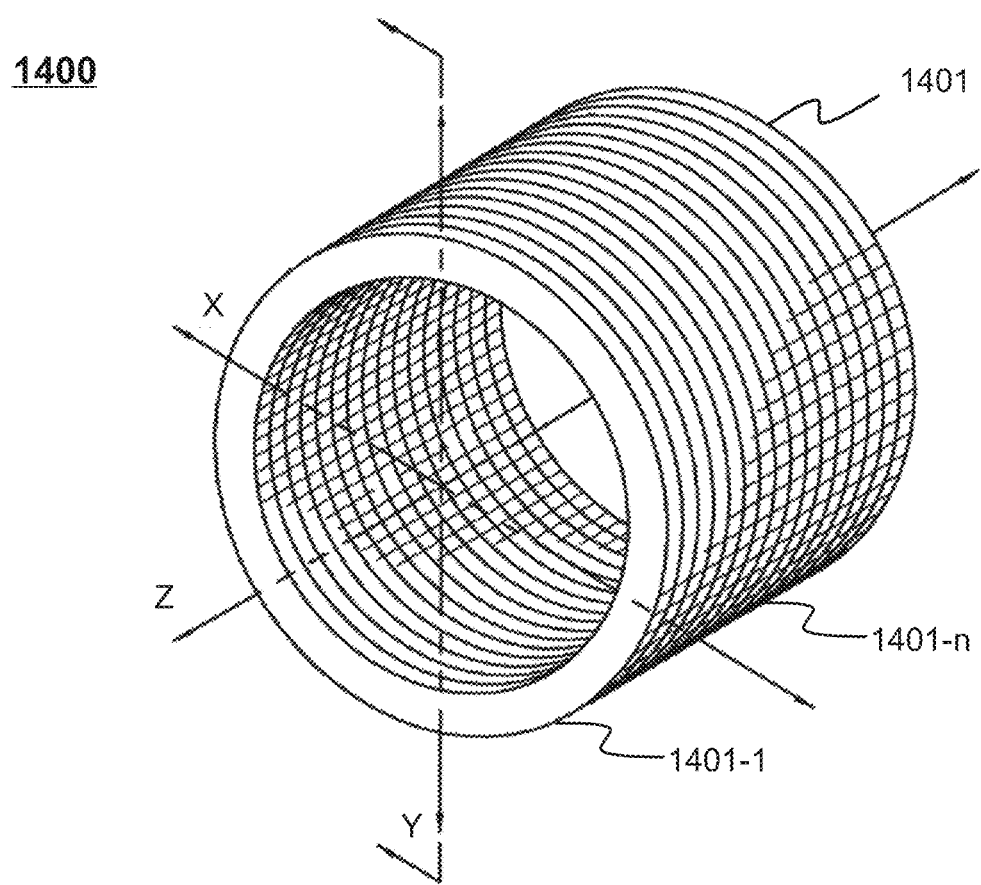
FIG. 14a is a schematic diagram illustrating an exemplary detector according to some embodiments of the present disclosure.
Figure 14B:
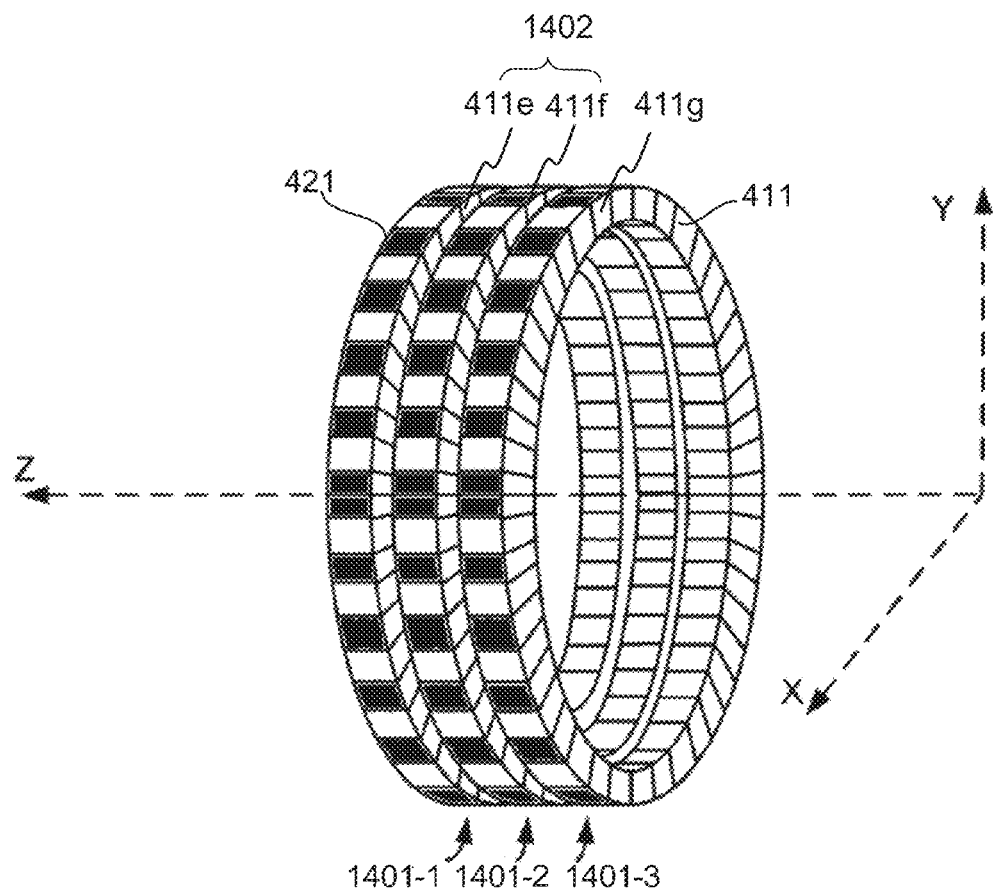
FIG. 14b is a schematic diagram illustrating an exemplary detector according to some embodiments of the present disclosure.

FIG. 14a is a schematic diagram illustrating an exemplary detector 1400 according to some embodiments of the present disclosure. FIG. 14b illustrates a perspective view of a part of the detector 1400 according to some embodiments of the present disclosure.

As illustrated, the detector 1400 may include a plurality of detector rings 1401 (e.g., detector rings 1401-1 to 1401-n) arranged along an axial direction (also referred to as the Z axis direction) of the detector 1400. The detector rings 1401 may form a scanning channel configured to accommodate an object to be examined. The detector ring 1401 may have any suitable configuration. For example, each detector ring 1401 may form a complete circle as shown in FIG. 14a. Alternatively, a detector ring 1401 may form an incomplete circle. In some embodiments, the detector ring 1401 may include two or more curved detector arrays. For example, each detector ring 1401 may be formed by one or more pairs of curved detector arrays spaced apart from each other by a distance. Each pair of curved detector arrays may be arranged in an opposing configuration. In some embodiments, the configurations of different detector rings 1401 in the detector 1400 may be the same or different.

As illustrated in FIG. 14b, a detector ring 1401 (e.g., the detector ring 1401-1) may include a plurality of crystal elements 411 and a plurality of photon-sensors 421. The crystal elements 411 may be arranged circumferentially along the peripheral direction of the detector ring 1401. Each crystal element 411 may include a proximal end and a distal end with respect to a central axis Z of the detector 1400 and extend along an extension direction from its distal end to its proximal end. The proximal end of a crystal element 411 may be close to the central axis and configured to receive radiation rays (e.g., gamma rays caused by annihilation events) from the scanning region. The distal end of a crystal element 411 may be far from the central axis and optically coupled with a photon-sensor 421 (shown as a darkened area in FIG. 14b).

In some embodiments, a photon-sensor 421 may be optically coupled with one or more crystal elements 411 of a detector ring 1401. Different photon-sensors 421 may be coupled with the same number/count of or different numbers/counts of crystal elements 411. For example, each photon-sensor 421 may be coupled with two adjacent crystal elements 411 in a detector ring 1401 along the circumferential direction of the detector ring 1401. In some embodiments, the plurality of photon-sensors 421 may form a plurality of photon-sensor rows along the Z axis direction as illustrated in FIG. 14b. In some embodiments, a coincidence event detected by photon-sensors 421 of a same detector ring 1401 may be referred to as a direct coincidence, and the coincidence event may define a direct plane. A coincidence event detected by photon-sensors 421 of different rings 1401 may be referred to as a cross coincidence, and the coincidence event may define a cross plane. A direct plane may be parallel or substantially parallel to the X-Y plane illustrated in FIG. 14a and a cross plane may have a certain angle with the X-Y plane.

In some embodiments, the crystal elements 411 may form a plurality of crystal groups 1402 arranged along the Z axis. The crystal group 1402 may be similar to the crystal group 430, except for certain components or features. Each crystal group 1402 may include at least two crystal elements 411 that belong to at least two individual detector rings 1401. For example, as illustrated in FIG. 14b, a crystal element 411e of the detector ring 1401-1 and a crystal element 411f of the detector ring 1401-2 may form a crystal group. As another example, a crystal element 411g of the detector ring 1401-3 and another crystal element 411 (not shown in FIG. 14b) in an adjacent detector ring 1401 may form a crystal group.

Similar to the crystal group 430 illustrated in FIGS. 4 to 6b and the description thereof, one or more first optical separators 412 and second optical separators 413 (not shown in FIGS. 14a and 14b) may be used in and/or between the crystal groups 1402, in order to control the light transmission between and within the crystal groups 1402. For example, a first optical separator 412 of a first length may be disposed or located between two adjacent crystal groups 1402. A second optical separator 413 of a second length may be disposed or located between two adjacent crystal elements 411 of a crystal group 1402. The first length of the first optical separator may be greater than the second length of the second optical separator. As used herein, the length of an optical separator of two adjacent crystal groups 1402 may refer to its length along an extension direction (or the third direction) of at least one crystal element 411 of the two adjacent crystal groups 1402. More descriptions of the first optical separator 412 and the second optical separator 413 may be found elsewhere in the present disclosure (e.g., FIG. 4 and the descriptions thereof).

In some embodiments, to control the light transmission between two adjacent crystal elements 411 of a detector ring 1401, one or more third optical separators 1140 (not shown in FIGS. 14a and 14b) may be applied. For example, a third optical separator 1140 (not shown) may be located between each pair of adjacent crystal elements 411 of each detector ring 1401. More descriptions of the third optical separator 1140 may be found elsewhere in the present disclosure (e.g., FIGS. 11a and 11b and the descriptions thereof).

It should be noted that the detector 1400 shown in FIGS. 14a and 14b are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, a detector 1400 may include any number/count of detector rings 1401. For example, the detector 1400 may include 16, 32, 64, or 96 detector rings. In some embodiments, a crystal group 1402 may include any number/count of crystal elements 411 arranged along the Z axis direction. For example, the crystal elements 411e, 411f, and 411g may form a crystal group.

Figure 15:
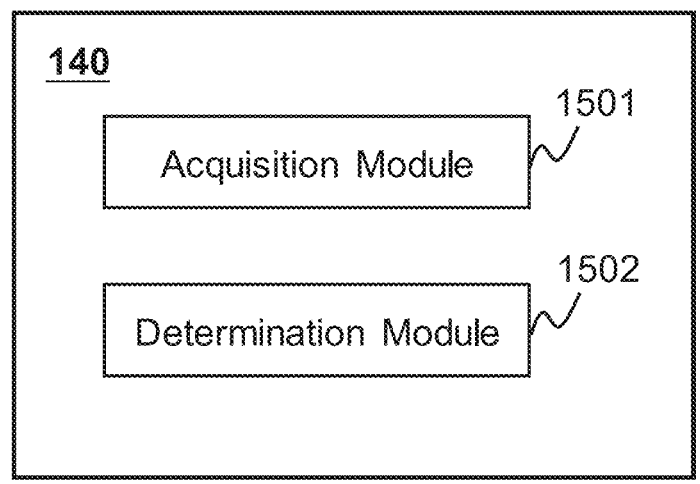
FIG. 15 is a block diagram illustrating an exemplary computing device according to some embodiments of the present disclosure.

FIG. 15 is a block diagram illustrating an exemplary computing device 140 according to some embodiments of the present disclosure. As shown in FIG. 15, the computing device 140 may include an acquisition module 1501 and a determination module 1502.

The acquisition module 1501 may be configured to obtain information used to determine the position of a photon gamma interaction in a crystal group. For example, the acquisition module 1501 may obtain output information of a plurality of photon-sensors optically coupled with the crystal group. As another example, the acquisition module 1501 may obtain a look-up table that records a relationship between depths of the photon gamma interaction and the output information of the photon-sensors. In some embodiments, the acquisition module 1501 may obtain information from one or more components of the imaging system 100, such as the PET imaging device 110, the storage device 150. Additionally or alternatively, the acquisition module 1501 may obtain information from an external source via the network 120.

The determination module 1502 may be configured to determine the position of a photon gamma interaction in a crystal group. For example, the determination module 1502 may determine a target crystal element in which the photon gamma interaction occurs in the crystal group. As another example, the determination module 1502 may determine the depth of the photon gamma interaction in the target crystal element. In some embodiments, the determination module 1502 may take an ICS phenomenon into consideration in the determination of the photon gamma interaction position. More descriptions regarding the determination of the photon gamma interaction position may be found elsewhere in the present disclosure. See, e.g., FIGS. 16 and 17 and relevant descriptions thereof.

It should be noted that the above description regarding the computing device 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the computing device 140 may include a storage module configured to store data generated by the above-mentioned modules of the computing device 140. As another example, one or more modules may be integrated into a single module to perform the functions thereof. Merely by way of example, the acquisition module 1501 and the determination module 1502 may be integrated into a module to acquire and analyze information.

FIG. 16 is a flowchart illustrating an exemplary process for determining a position of a photon gamma interaction in a crystal group according to some embodiments of the present disclosure. In some embodiments, one or more operations of the process 1600 illustrated in FIG. 16 may be implemented in the imaging system 100 illustrated in FIG. 1. For example, the process 1600 illustrated in FIG. 16 may be stored in the storage device 150 in the form of instructions, and invoked and/or executed by the computing device 140.

In 1601, the acquisition module 1501 may obtain output information of a first photon-sensor and a second photon-sensor. The first photon-sensor and the second photon-sensor may be optically coupled with a crystal group (e.g., the crystal group 430, the crystal group 1402, or the crystal group 900) as described elsewhere in this disclosure. The crystal group may include a plurality of crystal elements. Each of the first and second photon-sensors may be optically coupled with one or more of the crystal elements. For example, the crystal group may include two crystal elements, each of which may be optically coupled with the first photon-sensor and the second photon-sensor, respectively.

When a photon gamma interaction occurs in the crystal group coupled with the first and second photon-sensors, it may excite one or more optical photons, which may in turn be detected by the first photon-sensor and/or the second photon-sensor. In response to the detected optical photons, the first and the second photon-sensors may output electrical signals, which are referred to as the output information herein. The output information may include first output information of the first photon-sensor and second output information of the second photon-sensor. In some embodiments, the first or the second output information may include a value of the energy detected by the corresponding first or second photon-sensor. Alternatively, the output information of the first or the second photon-sensor may be a parameter other than the energy value, such as a signal intensity, a pulse width. The determination module 1502 may determine the corresponding energy value based on the output information.

In 1602, the determination module 1502 may identify, in the crystal group, a target crystal element in which the photon gamma interaction occurs based on the output information. In some embodiments, the target crystal element in the crystal group may be determined by comparing the energy detected by the first photon-sensor and the second photon-sensor. The target crystal element may be the one whose corresponding photon-sensor detects the greatest energy. For example, if the output information shows that the first photon-sensor detects greater energy than the second photon-sensor, the crystal element(s) corresponding to the first photon-sensor may be regarded as the target crystal element. In some embodiments, the first or the second photon-sensor may correspond to a plurality of crystal elements, and it may be possible that the target crystal element accordingly may include a plurality of crystal elements.

In 1603, the determination module 1502 may determine, based on the output information, a depth of the photon gamma interaction within the target crystal element. The depth of the photon gamma interaction (or DOI) within the target crystal element may refer to a distance between the photon gamma interaction and the first end S1 of the target crystal element along the extension direction of the target crystal element. In some embodiments, the depth may be determined based on a ratio of the energy detected by the first photon-sensor to the energy detected by the second photon-sensor. For example, the depth d of the photon gamma interaction within the target crystal element may be determined according to Equation (1):

$$d=LUT[E1/(E1+E2)] \qquad (1),$$

where E1 represents the energy detected by the first photon-sensor; E2 represents the energy detected by the second photon-sensor; and LUT represents an operation of looking up a lookup table. The lookup table may refer to a table that records a relationship between depths of photon gamma interactions in a target crystal element and values of E1/(E1+E2). In some embodiments, the lookup table may be determined based on a plurality of depths of photon gamma interactions and their corresponding values of E1/(E1+E2). The lookup table may be stored in a storage device (e.g., the storage device 150) of the imaging system 100. In the determination of the depth, the computing device 140 may retrieve the lookup table from the storage device and determine the depth d of the photon gamma interaction by consulting the lookup table.

It should be noted that the above description of the process 1600 is merely provided for the purpose of illustration, and not intended to limit the scope of the present disclosure. For persons having ordinary skills in the art, multiple variations and modifications may be made to the process 1600 under the teachings of the present disclosure. However, those variations and modifications do not depart from the scope of the present disclosure. In some embodiments, output information of two or more photon-sensors may be obtained in 1601. The two or more photon-sensors may be optically coupled with a crystal group (e.g., the crystal group 430, the crystal group 1402) as described elsewhere in this disclosure. The position of the photon gamma interaction may be determined based on the output information by performing operations 1602 and 1603. In some embodiments, as described in connection with FIGS. 9a and 9b, the DOI of a photon gamma interaction occurred within a crystal group (e.g., the crystal group 900) may be determined based on the time when the first photon-sensor and the second photon-sensor detected the corresponding photons.

FIG. 17 is a flowchart illustrating an exemplary process for determining a position of a photon gamma interaction according to some embodiments of the present disclosure. In some embodiments, one or more operations of the process 1700 illustrated in FIG. 17 may be implemented in the imaging system 100 illustrated in FIG. 1. For example, the process 1700 illustrated in FIG. 17 may be stored in the storage device 150 in the form of instructions, and invoked and/or executed by the computing device 140. In some embodiments, the process 1700 may be an example of the process 1600 when an ICS phenomenon is considered.

In 1701, the acquisition module 1501 may obtain output information of a plurality of photon-sensor groups. Each of the photon-sensor groups may include two or more photon-sensors and be optically coupled with a crystal group (e.g., the crystal group 430, the crystal group 1402) of a detector. The output information may include output information of the photon-sensor groups, and relate to a photon gamma interaction that occurs in the crystal groups.

In 1702, the determination module 1502 may determine, based on the output information, a plurality of candidate positions of the photon gamma interaction in the crystal groups. A candidate position may correspond to one of the plurality of crystal groups. A candidate position corresponding to a crystal group may include a candidate target crystal element in which the photon gamma interaction may have occurred and/or a candidate depth of the photon gamma interaction in the crystal group. In some embodiments, for each crystal group, the determination module 1502 may determine a position of the photon gamma interaction in the crystal group based on the output information of the corresponding photon-sensor group by implementing at least part of the process 1600. The determination module 1502 may then designate the position in each crystal group as one candidate position.

In 1703, the determination module 1502 may determine that an ICS occurs within the crystal groups based on the output information. In some embodiments, the determination module 1502 may determine whether the ICS occurs within the crystal groups based on the output information of each photon-sensor group and an energy of an annihilation photon involved in the photon gamma interaction. For example, if a sum of energy detected by one or more of the photon-sensor groups is equal to the energy of the annihilation photon, the determination module 1502 may determine that an ICS occurs within the plurality of crystal groups.

In 1704, the determination module 1502 may designate, among the plurality of candidate positions, the candidate position with the smallest candidate depth as a position of the photon gamma interaction. Because back scatter rarely occurs, the candidate position with the smallest candidate depth may be closest to the scanned object and correspond to a crystal element from which the annihilation photon initially enters, and therefore it may be deemed as the position of the photon gamma interaction.

It should be noted that the above description of the process 1700 is merely provided for the purpose of illustration, and not intended to limit the scope of the present disclosure. For persons having ordinary skills in the art, multiple variations and modifications may be made to the process 1700 under the teachings of the present disclosure. However, those variations and modifications do not depart from the scope of the present disclosure. For example, operations 1702 and 1703 may be performed simultaneously or operation 1703 may be performed before operation 1702.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as JAVA, SCALA, SMALLTALK, EIFFEL, JADE, EMERALD, C++, C#, VB. NET, PYTHON or the like, conventional procedural programming languages, such as the "C" programming language, Visual Basic, Fortran 2013, PERL, COBOL 2012, PHP, ABAP, dynamic programming languages such as PYTHON, RUBY, and GROOVY, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximately," or "substantially." For example, "about," "approximately," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

Certain embodiments of the present invention are directed to imaging systems. More particularly, some embodiments of the invention provide systems for medical imaging. Merely by way of example, some embodiments of the invention have been applied to positron emission tomography detectors. But it would be recognized that the invention has a much broader range of applicability.

As discussed above and further emphasized here, FIG. 9b is merely an example, which should not unduly limit the scope of the claims. One of ordinary skill in the art would recognize many variations, alternatives, and modifications. As shown in FIG. 9b, a crystal pair (e.g., a crystal group including two crystal elements) is coupled to a light bridge (e.g., light transmission medium 902 of an optical window), according to some embodiments of the present invention. Although the above has been shown using a selected group of components, there can be many alternatives, modifications, and variations. For example, some of the components may be expanded and/or combined. Other components may be inserted to those noted above. Depending upon the embodiment, the arrangement of components may be interchanged with others replaced.

In certain embodiments, a light bridge of a crystal pair is an internal light bridge with no optical interface between the internal light bridge and a first crystal of the crystal pair nor between the internal light bridge and a second crystal of the crystal pair. For example, a crystal pair with an internal light bridge may be formed by cutting a crystal block from a first end up to the internal light bridge, which has a height from a second end of the crystal block, thus defining the first crystal and the second crystal each on one side of the cut, with the internal light bridge at the second end connecting the first crystal and second crystal. As an example, the first crystal and the second crystal are physically separated by an optical separator (e.g., an optical shield) and connected by the internal light bridge (e.g., at a second end).

In some embodiments, a light bridge of a crystal pair is an external light bridge with an optical interface between the external light bridge and the first crystal of the crystal pair and between the external light bridge and the second crystal of the crystal pair. For example, a crystal pair with an external light bridge may be formed by coupling (e.g., adhering such as with optical glue) the first crystal and the crystal together with the external light bridge at the second end such that three separate pieces are coupled. As an example, the first crystal and the second crystal are physically separated by an optical separator (e.g., an optical shield) and connected by the external light bridge (e.g., at a second end). In certain examples, an external light bridge is configured to create a substantially seamless interface between the external light bridge and the crystal pair. A seamless interface may increase sensitivity and/or accuracy of the predicting of a coordinate of a scintillation event occurs in the crystal pair. In some examples, an external light bridge is configured to create a reflective surface at the interface between the external light bridge and the crystal pair. In certain examples, the reflective surface is configured to assist light radiation to travel from one crystal to another crystal in the crystal pair.

In various embodiments, the detector 112 for detecting a three-dimensional position of a scintillation event converting a gamma radiation into a visible radiation or visible photons includes a crystal array 410 including a plurality of crystal elements 411 arranged at least along a first direction and a second direction, and a photon-sensor array 420 including a plurality of photon-sensors 421 arranged at least along the first direction and the second direction. In some examples, the plurality of crystal elements 411 extends along a third direction between a first end S1 and a second end S2. In certain examples, the plurality of crystal elements 411 is configured to receive the gamma radiation entered from the second end S2. In various examples, the plurality of photon-sensors 421 is configured to receive the visible radiation or visible photons at the first end S1. In some examples, the plurality of crystal elements 411 is arranged into a plurality of crystal groups 430. In certain examples, each of the plurality of crystal groups 430 is optically coupled to one light transmission medium 902 of an optical window at the second end S2 extending and bridging the visible radiation or visible photons along the first direction. In various examples, each crystal group of the plurality of crystal groups 430 includes two crystal elements. For example, one crystal group includes crystal 411a and crystal 411b. In some examples, the two crystal elements in each crystal group are arranged side-by-side along the first direction and optically coupled for the visible radiation or visible photons along the first direction through only the light transmission medium 902 of the optical window coupled to each crystal group. In certain examples, the light transmission medium 902 of each optical window is optically shielded for the light along the second direction. In various examples, plurality of crystal groups 430 is arranged side-by-side along at least the second direction. In some examples, each of the plurality of crystal groups 430 is optically coupled for the visible radiation or visible photons in the second direction with at least a neighboring crystal group only through two light tunnels. For example, a crystal column is optically coupled for the visible radiation or visible photons in the second direction only through a first light tunnel 1172a and a second light tunnel 1172b (e.g., see FIG. 11a). In certain examples, each light tunnel of the two light tunnels is optically shielded for the visible radiation or visible photons along the first direction. For example, the first light tunnel 1172a and a second light tunnel 1172b are each optically shielded for the visible radiation or visible photons along the first direction. In some examples, a light tunnel group corresponds to each crystal group. In various examples, each light tunnel optically couples one crystal element of each crystal group with one crystal element of a neighboring crystal group for the visible radiation or visible photons in the second direction. In some examples, the plurality of photon-sensors 421 is arranged into a plurality of photon-sensor groups. In certain examples, each of the plurality of photon-sensor groups includes two photon-sensors, such as only the two photon-sensors. In various examples, the two photon-sensors in each photon-sensor group are arranged side-by-side along the first direction. In some examples, one photon-sensor group of the plurality of photon-sensor groups includes a first photon-sensor 421a and a second photon-sensor 421b. In certain examples, one crystal group of the plurality of crystal groups 430 includes a first crystal 411a and a second crystal 411b. In various examples, the first photon-sensor 421a corresponds to the first crystal 411a and the second photon-sensor 421b corresponds to the second crystal 411b.

In some embodiments, each crystal element of the plurality of crystal elements 411 (e.g., see FIG. 11a) is bounded by one or more separators extending along the third direction. In some examples, the one or more separators is configured to shield at least the visible radiation or visible photons.

In some embodiments, the one or more separators includes a first optical separator 412 (e.g., see FIG. 11a) arranged at an interface between two neighboring crystal groups of the plurality of crystal groups 430 along the first direction. In some examples, the first optical separator 412 extends from the first end S1 to the second end S2 to optically shield the two neighboring crystal groups along the first direction.

In some embodiments, the one or more separators includes a second optical separator 413 arranged at an interface between the first crystal 411a and the second crystal 411b included in the one crystal group of the plurality of crystal groups 430. In some examples, the second optical separator 413 (e.g., see FIG. 11a) extends from the first end S1 towards the second end S2 until reaching the light transmission medium 902 of the optical window optically coupling the first crystal 411a and the second crystal 411b.

In some embodiments, the one or more separators includes a third optical separator 414 arranged at an interface between two neighboring crystal groups of the plurality of crystal groups 430 along the second direction. In some examples, the third optical separator 414 extends from the second end S2 towards the first end S1 until reaching the light tunnel (e.g., light tunnel 1172a or light tunnel 1172b) optically coupling the two neighboring crystal groups along the second direction.

In some embodiments, the light transmission medium 902 of the optical window optically coupling the two crystal elements (e.g., crystal 421a and crystal 421b) in each crystal group is of an internal optical window configured to be optically transparent for the visible radiation or visible photons when traveling between the two crystal elements.

In some embodiments, the light transmission medium 902 of the optical window optically coupling the two crystal elements (e.g., crystal 421a and crystal 421b) in each crystal group is of an external optical window configured to create an optical interface for the visible radiation or visible photons when traveling between the two crystal elements.

In some embodiments, the light transmission medium 902 of the optical window optically coupling the two crystal elements (e.g., crystal 421a and crystal 421b) in each crystal group comprises a scintillation material or a transmitting material.

In some embodiments, the first direction is orthogonal to the second direction, first direction is orthogonal to the third direction, and the second direction is orthogonal to the third direction.

In some embodiments, the first direction is nonlinear and is along at least part of a circle. For example, when the crystal array 410 includes a detector ring 1401 that forms a complete circle or an incomplete circle, the crystal array 410 is arranged along a first direction that is nonlinear.

In some embodiments, the plurality of crystal elements 411 is polished at the second end S2.

In various embodiments, the detector 112 for detecting one or more three-dimensional positions of one or more scintillation events converting a gamma radiation into a visible radiation or visible photons includes a crystal array 410 including a plurality of crystal elements 411 arranged in crystal rows along a first direction and in crystal columns along a second direction, and a photon-sensor array 420 including a plurality of photon-sensors 421 arranged in photon-sensor rows along the first direction and in photon-sensor columns along the second direction. In some examples, the plurality of crystal elements 411 extends along a third direction between a first end S1 and a second end S2. In certain examples, the plurality of crystal elements 411 is configured to receive the gamma radiation from the second end S2. In various examples, the plurality of photon-sensors 421 is configured to receive the visible radiation or visible photons at the first end S1. In some examples, one crystal row of the crystal rows includes one or more crystal groups 430 along the first direction. In certain examples, one crystal group of the one or more crystal groups includes a first crystal element (e.g., crystal 411a) and a second crystal element (e.g., crystal 411b). In various examples, one photon-sensor row of the photon-sensor rows includes one or more photon-sensor groups along the first direction. In some examples, one light photon-sensor group of the one or more photon-sensor groups includes a first photon-sensor (e.g., photon-sensor 421a) and a second photon-sensor (e.g., photon-sensor 421b). In certain examples, the first photon-sensor (e.g., photon-sensor 421a) corresponds to the first crystal element (e.g., crystal 411a). In various examples, the second photon-sensor (e.g., photon-sensor 421b) corresponds to the second crystal element (e.g., crystal 411b). In some examples, the one photon-sensor group is configured to determine whether the scintillation event occurs within the first crystal element (e.g., crystal 411a) or within the second crystal element (e.g., crystal 411b) and/or determine the position of the scintillation event along the third direction. In certain examples, one crystal column of the crystal columns includes multiple crystal elements along the second direction. In various examples, one photon-sensor column of the photon-sensor columns includes multiple photon-sensors along the second direction. In some examples, the one photon-sensor column corresponds to the one crystal column. In certain examples, the one photon-sensor column is configured to determine within which crystal element of the multiple crystal elements the scintillation event occurs.

In some embodiments, the first photon-sensor 421a is configured to obtain a first energy, the second photon-sensor 421b is configured to obtain a second energy, and the one photon-sensor group is configured to determine whether the position of a scintillation event is within the first crystal 411a or within the second crystal 411b based at least in part on the first energy and the second energy.

In some embodiments, the one photon-sensor group is further configured to determine the position of the scintillation event along the third direction based at least in part on the first energy and the second energy based at least in part on determining the location of the scintillation event to be in the first crystal 411a if the first energy is greater than the second energy and determining the location of the scintillation event to be in the second crystal 411b if the first energy is less than the second energy.

In some embodiments, the first photon-sensor 421a is configured to obtain a first energy, the second photon-sensor 421b is configured to obtain a second energy, and the one photon-sensor group is configured to determine the position of the scintillation event along the third direction based at least in part on the first energy and the second energy.

In some embodiments, the one photon-sensor group is further configured to determine the position of the scintillation event along the third direction based at least in part on calculating an energy ratio based at least in part on the first energy and the second energy and determining the position of the scintillation event along the third direction based at least in part on the energy ratio and a look-up-table.

In some embodiments, the one photon-sensor group is further configured to determine the position of the scintillation event along the third direction based at least in part on calculating an energy ratio based at least in part on the first energy and the second energy and determining the position of the scintillation event along the third direction based at least in part on a distance ratio between a first path and a second path. The first path is from the position of the scintillation event to the first photon-sensor 421a, and the second path is from the position of the scintillation event to the second photon-sensor 421b.

In some embodiments, the crystal array 410 includes a first crystal group A1/B1 and a second crystal group A3/B3, and the photon-sensor array 420 includes a first photon-sensor group and a second photon-sensor group. In some examples, the first photon-sensor group is configured to determine a first three-dimensional position of a first scintillation event within the first crystal group A1/B1. In certain examples, the first three-dimensional position includes a first depth along the third direction. In some examples, the second photon-sensor group is configured to determine a second three-dimensional position of a second scintillation event within the second crystal group A3/B3. In certain examples, the second three-dimensional position includes a second depth along the third direction. In various examples, the first photon-sensor group and the second photon-sensor group are configured to determine the first scintillation event occurs before the second scintillation event in response to the first depth being smaller than the second depth and/or determine the first scintillation event occurs after the second scintillation event in response to the first depth being larger than the second depth.

In some embodiments, the photon-sensor array 420 is configured to generate an event coordinate corresponding to the position of the scintillation event based at least in part on the determined crystal element within which the scintillation event occurs and the determined position of the scintillation event along the third direction.

In various embodiments, the detector 112 for detecting a three-dimensional position of a scintillation event converting a gamma radiation into a visible radiation or visible photons includes a crystal group and a photon-sensor group. In some examples, the crystal group includes a first crystal 411a and a second crystal 411b. In certain examples, the first crystal 411a and the second crystal 411b are arranged side-by-side along a first direction. In various examples, the first crystal 411a and the second crystal 411b extend along a third direction between a first end S1 and a second end S2. In some examples, the first crystal 411a and the second crystal 411b are configured to receive the gamma radiation entered from the second end S2. In certain examples, the crystal group is optically coupled to the light transmission medium 902 of the optical window at the second end S2 extending and bridging the visible radiation or visible photons along the first direction. In various examples, the first crystal 411a and the second crystal 411b are optically coupled for the visible radiation or visible photons along the first direction through only the light transmission medium 902 of the optical window. In some examples, the photon-sensor group includes a first photon-sensor 421a corresponding to the first crystal 411a and a second photon-sensor 421b corresponding to the second crystal 411b. In certain examples, the first photon-sensor 421a and the second photon-sensor 421b are configured to receive the visible radiation or visible photons at the first end S1. In various examples, the first photon-sensor 421a and the second photon-sensor 421b are arranged side-by-side along the first direction.

In various embodiments, a system (e.g., detector 112) for detecting a three-dimensional position of a scintillation event converting a radiation (e.g., gamma radiation) into a light (e.g., visible radiation or visible photons) includes a crystal array (e.g., crystal array 410) including a plurality of crystal elements (e.g., plurality of crystal elements 411) arranged at least along a first direction and a second direction, and a light sensor array (e.g., photon-sensor array 420) including a plurality of light sensors (e.g., plurality of photon-sensors 421) arranged at least along the first direction and the second direction. In some examples, the plurality of crystal elements (e.g., plurality of crystal elements 411) extends along a third direction between a first end (e.g., first end S1) and a second end (e.g., second end S2). In certain examples, the plurality of crystal elements (e.g., plurality of crystal elements 411) is configured to receive the radiation (e.g., gamma radiation) entered from the second end (e.g., second end S2). In various examples, the plurality of light sensors (e.g., plurality of photon-sensors 421) is configured to receive the light (e.g., visible radiation or visible photons) at the first end (e.g., first end S1). In some examples, the plurality of crystal elements (e.g., plurality of crystal elements 411) is arranged into a plurality of crystal pairs (e.g., plurality of crystal groups 430). In certain examples, each of the plurality of crystal pairs (e.g., plurality of crystal groups 430) is optically coupled to one light bridge (e.g., the light transmission medium 902 of the optical window) at the second end (e.g., second end S2) extending and bridging light (e.g., visible radiation or visible photons) along the first direction. In various examples, each of the plurality of crystal pairs (e.g., plurality of crystal groups 430) includes two crystal elements (e.g., crystal 411a and crystal 411b). In some examples, the two crystal elements in each crystal pair (e.g., crystal group) are arranged side-by-side along the first direction and optically coupled for the light (e.g., visible radiation or visible photons) along the first direction through only the one light bridge (e.g., the light transmission medium 902 of the optical window) coupled to each crystal pair (e.g., crystal group). In certain examples, each light bridge (e.g., the light transmission medium 902 of the optical window) is optically shielded for the light along the second direction. In various examples, the plurality of crystal pairs (e.g., plurality of crystal groups 430) is arranged side-by-side along at least the second direction. In some examples, each of the plurality of crystal pairs (e.g., plurality of crystal groups 430) is optically coupled for the light (e.g., visible radiation or visible photons) in the second direction with at least a neighboring crystal pair (e.g., crystal group) only through two light tunnels (e.g., light tunnel 1172a and light tunnel 1172b). In certain examples, each light tunnel of the two light tunnels (e.g., light tunnel 1172a and light tunnel 1172b) is optically shielded for the light (e.g., visible radiation or visible photons) along the first direction. In various examples, each of the two light tunnels (e.g., light tunnel 1172a and light tunnel 1172b) optically couples one crystal element of each crystal pair (e.g., crystal group) with one crystal element of a neighboring crystal pair (e.g., crystal group) for the light (e.g., visible radiation or visible photons) in the second direction. In some examples, the plurality of light sensors (e.g., plurality of photon-sensors 421) is arranged into a plurality of light sensor pairs (e.g., plurality of photon-sensor groups). In certain examples, each of the plurality of light sensor pairs (e.g., plurality of photon-sensor groups) includes two light sensors (e.g., photon-sensors). In various examples, the two light sensors (e.g., photon-sensors) in each light sensor pair (e.g., photon-sensor group) are arranged side-by-side along the first direction. In some examples, one light sensor pair of the plurality of light sensor pairs (e.g., plurality of photon-sensor groups) includes a first light sensor (e.g., photon-sensor 421a) and a second light sensor (e.g., photon-sensor 421b). In certain examples, one crystal pair (e.g., crystal group) of the plurality of crystal pairs (e.g., plurality of crystal groups 430) includes a first crystal element (e.g., crystal 411a) and a second crystal element (e.g., crystal 411b). In various examples, the first light sensor (e.g., photon-sensor 421a) corresponds to the first crystal element (e.g., crystal 411a) and the second light sensor (e.g., photon-sensor 421b) corresponds to the second crystal element (e.g., crystal 411b).

In some embodiments, each crystal element of the plurality of crystal elements (e.g., plurality of crystal elements 411) is bounded by a plurality of optical shields (e.g., one or more separators) extending along the third direction. In some examples, the plurality of optical shields (e.g., one or more separators) is configured to shield at least the light (e.g., visible radiation or visible photons).

In some embodiments, the plurality of optical shields (e.g., one or more separators) includes a first optical shield (e.g., first optical separator 412) arranged at an interface between two neighboring crystal pairs (e.g., crystal groups) of the plurality of crystal pairs (e.g., plurality of crystal groups 430) along the first direction. In some examples, the first optical shield (e.g., first optical separator 412) extends from the first end (e.g., first end S1) to the second end (e.g., second end S2) to optically shield the two neighboring crystal pairs (e.g., crystal groups) along the first direction.

In some embodiments, the plurality of optical shields (e.g., one or more separators) includes a second optical shield (e.g., second optical separator 413) arranged at an interface between the first crystal element (e.g., crystal 411a) and the second crystal element (e.g., crystal 411b) included in the one crystal pair (e.g., crystal group) of the plurality of crystal pairs (e.g., plurality of crystal groups 430). In some examples, the second optical shield (e.g., second optical separator 413) extends from the first end (e.g., first end S1) towards the second end (e.g., second end S2) until reaching the light bridge (e.g., the light transmission medium 902 of the optical window) optically coupling the first crystal element (e.g., crystal 411a) and the second crystal element (e.g., crystal 411b).

In some embodiments, the plurality of optical shields (e.g., one or more separators) includes a third optical shield (e.g., third optical separator 414) arranged at an interface between two neighboring crystal pairs (e.g., crystal groups) of the plurality of crystal pairs (e.g., plurality of crystal groups 430) along the second direction. In some examples, the third optical shield (e.g., third optical separator 414) extends from the second end (e.g., second end S2) towards the first end (e.g., first end S1) until reaching the light tunnel (e.g., light tunnel 1172a) optically coupling the two neighboring crystal pairs (e.g., crystal groups) along the second direction.

In some embodiments, the light bridge (e.g., the light transmission medium 902 of the optical window) optically coupling the two crystal elements (e.g., crystal 421a and crystal 421b) in each crystal pair (e.g., crystal group) is an internal light bridge (e.g., of an internal optical window) configured to be optically transparent for the light (e.g., visible radiation or visible photons) when traveling between the two crystal elements.

In some embodiments, the light bridge (e.g., the light transmission medium 902 of the optical window) optically coupling the two crystal elements (e.g., crystal 421a and crystal 421b) in each crystal pair (e.g., crystal group) is an external light bridge (e.g., of an external optical window) configured to create an optical interface for the light (e.g., visible radiation or visible photons) when traveling between the two crystal elements.

In some embodiments, the light bridge (e.g., the light transmission medium 902 of the optical window) optically coupling the two crystal elements (e.g., crystal 421a and crystal 421b) in each crystal pair (e.g., crystal group) comprises a scintillation material or a transmitting material.

In some embodiments, the first direction is orthogonal to the second direction, first direction is orthogonal to the third direction, and the second direction is orthogonal to the third direction.

In some embodiments, the first direction is nonlinear and is along at least part of a circle (e.g., when the crystal array 410 includes a detector ring 1401 that forms a complete circle or an incomplete circle).

In some embodiments, the plurality of crystal elements (e.g., the plurality of crystal elements 411) is polished at the second end (e.g., second end S2).

In various embodiments, a system (e.g., the detector 112) for detecting one or more three-dimensional positions of one or more scintillation events converting a radiation (e.g., gamma radiation) into a light (e.g., visible radiation or visible photons) includes a crystal array (e.g., crystal array 410) including a plurality of crystal elements (e.g., plurality of crystal elements 411) arranged in crystal rows along a first direction and in crystal columns along a second direction, and a light sensor array (e.g., photon-sensor array 420) including a plurality of light sensors (e.g., plurality of photon-sensors 421) arranged in light sensor rows (e.g., photon-sensor rows) along the first direction and in light sensor columns (e.g., photon-sensor columns) along the second direction. In some examples, the plurality of crystal elements (e.g., plurality of crystal elements 411) extends along a third direction between a first end (e.g., first end S1) and a second end (e.g., second end S2). In certain examples, the plurality of crystal elements (e.g., plurality of crystal elements 411) is configured to receive the radiation (e.g., gamma radiation) from the second end (e.g., second end S2). In various examples, the plurality of light sensors (e.g., plurality of photon-sensors 421) is configured to receive the light (e.g., visible radiation or visible photons) at the first end (e.g., first end S1). In some examples, one crystal row of the crystal rows includes one or more crystal pairs (e.g., one or more crystal groups) along the first direction. In certain examples, one crystal pair (e.g., crystal group) of the one or more crystal pairs (e.g., one or more crystal groups) includes a first crystal element (e.g., crystal 411a) and a second crystal element (e.g., crystal 411b). In various examples, one light sensor row (e.g., photon-sensor row) of the light sensor rows (e.g., photon-sensor rows) includes one or more light sensor pairs (e.g., one or more photon-sensor groups) along the first direction. In some examples, one light sensor pair (e.g., photon-sensor group) of the one or more light sensor pairs (e.g., one or more photon-sensor groups) includes a first light sensor (e.g., photon-sensor 421a) and a second light sensor (e.g., photon-sensor 421b). In certain examples, the first light sensor (e.g., photon-sensor 421a) corresponds to the first crystal element (e.g., crystal 411a). In various examples, the second light sensor (e.g., photon-sensor 421b) corresponds to the second crystal element (e.g., crystal 411b). In some examples, the one light sensor pair (e.g., photon-sensor group) is configured to determine whether the scintillation event occurs within the first crystal element (e.g., crystal 411a) or within the second crystal element (e.g., crystal 411b) and/or determine the position of the scintillation event along the third direction. In certain examples, one crystal column of the crystal columns includes multiple crystal elements along the second direction. In various examples, one light sensor column (e.g., photon-sensor column) of the light sensor columns (e.g., photon-sensor columns) includes multiple light sensors (e.g., photon-sensors) along the second direction. In some examples, the one light sensor column (e.g., photon-sensor column) corresponds to the one crystal column. In certain examples, the one light sensor column (e.g., photon-sensor column) is configured to determine within which crystal element of the multiple crystal elements the scintillation event occurs.

In some embodiments, the first light sensor (e.g., photon-sensor 421a) is configured to obtain a first energy, the second light sensor (e.g., photon-sensor 421b) is configured to obtain a second energy, and the one light sensor pair (e.g., photon-sensor group) is configured to determine whether the position of a scintillation event is within the first crystal element (e.g., crystal 411a) or within the second crystal element (e.g., crystal 411b) based at least in part on the first energy and the second energy.

In some embodiments, the one light sensor pair (e.g., photon-sensor group) is further configured to determine the position of the scintillation event along the third direction based at least in part on the first energy and the second energy based at least in part on determining the location of the scintillation event to be in the first crystal element (e.g., crystal 411a) if the first energy is greater than the second energy and determining the location of the scintillation event to be in the second crystal element (e.g., crystal 411b) if the first energy is less than the second energy.

In some embodiments, the first light sensor (e.g., first photon-sensor 421a) is configured to obtain a first energy, the second light sensor (e.g., second photon-sensor 421b) is configured to obtain a second energy, and the one light sensor pair (e.g., photon-sensor group) is configured to determine the position of the scintillation event along the third direction based at least in part on the first energy and the second energy.

In some embodiments, the one light sensor pair (e.g., photon-sensor group) is further configured to determine the position of the scintillation event along the third direction based at least in part on calculating an energy ratio based at least in part on the first energy and the second energy and determining the position of the scintillation event along the third direction based at least in part on the energy ratio and a look-up-table.

In some embodiments, the one light sensor pair (e.g., photon-sensor group) is further configured to determine the position of the scintillation event along the third direction based at least in part on calculating an energy ratio based at least in part on the first energy and the second energy and determining the position of the scintillation event along the third direction based at least in part on a distance ratio between a first path and a second path. The first path is from the position of the scintillation event to the first light sensor (e.g., photon-sensor 421a), and the second path is from the position of the scintillation event to the second light sensor (e.g., photon-sensor 421b).

In some embodiments, the crystal array (e.g., crystal array 410) includes a first crystal pair (e.g., crystal group A1/B1) and a second crystal pair (e.g., crystal group A3/B3), and the light sensor array (e.g., photon-sensor array 420) includes a first light sensor pair (e.g., first photon-sensor group) and a second light sensor pair (e.g., second photon-sensor group). In some examples, the first light sensor pair (e.g., first photon-sensor group) is configured to determine a first three-dimensional position of a first scintillation event within the first crystal pair (e.g., crystal group A1/B1). In certain examples, the first three-dimensional position includes a first depth along the third direction. In some examples, the second light sensor pair (e.g., second photon-sensor group) is configured to determine a second three-dimensional position of a second scintillation event within the second crystal pair (e.g., crystal group A3/B3). In certain examples, the second three-dimensional position includes a second depth along the third direction. In various examples, the first light sensor pair and the second light sensor pair (e.g., the first photon-sensor group and the second photon-sensor group) are configured to determine the first scintillation event occurs before the second scintillation event in response to the first depth being smaller than the second depth and/or determine the first scintillation event occurs after the second scintillation event in response to the first depth being larger than the second depth.

In some embodiments, the light sensor array (e.g., photon-sensor array 420) is configured to generate an event coordinate corresponding to the position of the scintillation event based at least in part on the determined crystal element within which the scintillation event occurs and the determined position of the scintillation event along the third direction.

In various embodiments, a system (e.g., the detector 112) for detecting a three-dimensional position of a scintillation event converting a radiation (e.g., gamma radiation) into a light (e.g., visible radiation or visible photons) includes a crystal pair (e.g., crystal group) and a light sensor pair (e.g., photon-sensor group). In some examples, the crystal pair (e.g., crystal group) includes a first crystal element (e.g., crystal 411a) and a second crystal element (e.g., crystal 411b). In certain examples, the first crystal element (e.g., crystal 411a) and the second crystal element (e.g., crystal 411b) are arranged side-by-side along a first direction. In various examples, the first crystal element (e.g., crystal 411a) and the second crystal element (e.g., crystal 411b) extend along a third direction between a first end (e.g., first end S1) and a second end (e.g., second end S2). In some examples, the first crystal element (e.g., crystal 411a) and the second crystal element (e.g., crystal 411b) are configured to receive the radiation (e.g., gamma radiation) entered from the second end (e.g., second end S2). In certain examples, the crystal pair (e.g., crystal group) is optically coupled to a light bridge (e.g., the light transmission medium 902 of the optical window) at the second end (e.g., second end S2) extending and bridging light (e.g., visible radiation or visible photons) along the first direction. In various examples, the first crystal element (e.g., crystal 411a) and the second crystal element (e.g., crystal 411b) are optically coupled for the light (e.g., visible radiation or visible photons) along the first direction through only the light bridge (e.g., the light transmission medium 902 of the optical window). In some examples, the light sensor pair (e.g., photon-sensor group) includes a first light sensor (e.g., photon-sensor 421a) corresponding to the first crystal element (e.g., crystal 411a) and a second light sensor (e.g., photon-sensor 421b) corresponding to the second crystal element (e.g., crystal 411b). In certain examples, the first light sensor (e.g., photon-sensor 421a) and the second light sensor (e.g., photon-sensor 421b) are configured to receive the light (e.g., visible radiation or visible photons) at the first end (e.g., first end S1). In various examples, the first light sensor (e.g., first photon-sensor 421a) and the second light sensor (e.g., second photon-sensor 421b) are arranged side-by-side along the first direction.

In various embodiments, a system for detecting a three-dimensional position of a scintillation event converting a radiation into a light includes a crystal array including a plurality of crystal elements arranged at least along a first direction and a second direction, and a light sensor array including a plurality of light sensors arranged at least along the first direction and the second direction. In some examples, the plurality of crystal elements extends along a third direction between a first end and a second end. In some examples, the plurality of crystal elements is arranged into a plurality of crystal pairs. In certain examples, each of the plurality of crystal pairs is optically coupled to one light bridge at the second end extending and bridging light along the first direction. In various examples, each of the plurality of crystal pairs includes two crystal elements. In some examples, the two crystal elements in each crystal pair are arranged side-by-side along the first direction and optically coupled for the light along the first direction through only the one light bridge coupled to each crystal pair. In certain examples, each light bridge is optically shielded for the light along the second direction. In various examples, the plurality of crystal pairs is arranged side-by-side along at least the second direction. In some examples, each of the plurality of crystal pairs is optically coupled for the light in the second direction with at least a neighboring crystal pair only through two light tunnels. In certain examples, each light tunnel of the two light tunnels is optically shielded for the light along the first direction. In various examples, each of the two light tunnels optically couples one crystal element of each crystal pair with one crystal element of a neighboring crystal pair for the light in the second direction. In some examples, the plurality of light sensors is arranged into a plurality of light sensor pairs. In certain examples, each of the plurality of light sensor pairs includes two light sensors. In various examples, the two light sensors in each light sensor pair are arranged side-by-side along the first direction. In some examples, one light sensor pair of the plurality of light sensor pairs includes a first light sensor and a second light sensor. In certain examples, one crystal pair of the plurality of crystal pairs includes a first crystal element and a second crystal element. In various examples, the first light sensor corresponds to the first crystal element and the second light sensor corresponds to the second crystal element.

In some embodiments, each crystal element of the plurality of crystal elements is bounded by a plurality of optical shields extending along the third direction. In some examples, the plurality of optical shields is configured to shield at least the light.

In some embodiments, the plurality of optical shields includes a first optical shield arranged at an interface between two neighboring crystal pairs of the plurality of crystal pairs along the first direction. In some examples, the first optical shield extends from the first end to the second end to optically shield the two neighboring crystal pairs along the first direction.

In some embodiments, the plurality of optical shields includes a second optical shield arranged at an interface between the first crystal element and the second crystal element included in the one crystal pair of the plurality of crystal pairs. In some examples, the second optical shield extends from the first end towards the second end until reaching the light bridge optically coupling the first crystal element and the second crystal element.

In some embodiments, the plurality of optical shields includes a third optical shield arranged at an interface between two neighboring crystal pairs of the plurality of crystal pairs along the second direction. In some examples, the third optical shield extends from the second end towards the first end until reaching the light tunnel optically coupling the two neighboring crystal pairs along the second direction.

In some embodiments, the light bridge optically coupling the two crystal elements in each crystal pair is an internal light bridge configured to be optically transparent for the light when traveling between the two crystal elements.

In some embodiments, the light bridge optically coupling the two crystal elements in each crystal pair is an external light bridge configured to create an optical interface for the light when traveling between the two crystal elements.

In some embodiments, the light bridge optically coupling the two crystal elements in each crystal pair comprises a scintillation material or a transmitting material.

In some embodiments, the first direction is orthogonal to the second direction, first direction is orthogonal to the third direction, and the second direction is orthogonal to the third direction.

In some embodiments, the first direction is nonlinear and is along at least part of a circle.

In some embodiments, the plurality of crystal elements is polished at the second end.

In various embodiments, a system for detecting one or more three-dimensional positions of one or more scintillation events converting a radiation into a light includes a crystal array including a plurality of crystal elements arranged in crystal rows along a first direction and in crystal columns along a second direction, and a light sensor array including a plurality of light sensors arranged in light sensor rows along the first direction and in light sensor columns along the second direction. In some examples, the plurality of crystal elements extends along a third direction between a first end and a second end. In some examples, one crystal row of the crystal rows includes one or more crystal pairs along the first direction. In certain examples, one crystal pair of the one or more crystal pairs includes a first crystal element and a second crystal element. In various examples, one light sensor row of the light sensor rows includes one or more light sensor pairs along the first direction. In some examples, one light sensor pair of the one or more light sensor pairs includes a first light sensor and a second light sensor. In certain examples, the first light sensor corresponds to the first crystal element. In various examples, the second light sensor corresponds to the second crystal element. In some examples, the one light sensor pair is configured to determine whether the scintillation event occurs within the first crystal element or within the second crystal element and/or determine the position of the scintillation event along the third direction. In certain examples, one crystal column of the crystal columns includes multiple crystal elements along the second direction. In various examples, one light sensor column of the light sensor columns includes multiple light sensors along the second direction. In some examples, the one light sensor column corresponds to the one crystal column. In certain examples, the one light sensor column is configured to determine within which crystal element of the multiple crystal elements the scintillation event occurs.

In some embodiments, the first light sensor is configured to obtain a first energy, the second light sensor is configured to obtain a second energy, and the one light sensor pair is configured to determine whether the position of a scintillation event is within the first crystal element or within the second crystal element based at least in part on the first energy and the second energy.

In some embodiments, the one light sensor pair is further configured to determine the position of the scintillation event along the third direction based at least in part on the first energy and the second energy based at least in part on determining the location of the scintillation event to be in the first crystal element if the first energy is greater than the second energy and determining the location of the scintillation event to be in the second crystal element if the first energy is less than the second energy.

In some embodiments, the first light sensor is configured to obtain a first energy, the second light sensor is configured to obtain a second energy, and the one light sensor pair is configured to determine the position of the scintillation event along the third direction based at least in part on the first energy and the second energy.

In some embodiments, the one light sensor pair is further configured to determine the position of the scintillation event along the third direction based at least in part on calculating an energy ratio based at least in part on the first energy and the second energy and determining the position of the scintillation event along the third direction based at least in part on the energy ratio and a look-up-table.

In some embodiments, the one light sensor pair is further configured to determine the position of the scintillation event along the third direction based at least in part on calculating an energy ratio based at least in part on the first energy and the second energy and determining the position of the scintillation event along the third direction based at least in part on a distance ratio between a first path and a second path. The first path is from the position of the scintillation event to the first light sensor, and the second path is from the position of the scintillation event to the second light sensor.

In some embodiments, the crystal array includes a first crystal pair and a second crystal pair, and the light sensor array includes a first light sensor pair and a second light sensor pair. In some examples, the first light sensor pair is configured to determine a first three-dimensional position of a first scintillation event within the first crystal pair. In certain examples, the first three-dimensional position includes a first depth along the third direction. In some examples, the second light sensor pair is configured to determine a second three-dimensional position of a second scintillation event within the second crystal pair. In certain examples, the second three-dimensional position includes a second depth along the third direction. In various examples, the first light sensor pair and the second light sensor pair are configured to determine the first scintillation event occurs before the second scintillation event in response to the first depth being smaller than the second depth and/or determine the first scintillation event occurs after the second scintillation event in response to the first depth being larger than the second depth.

In some embodiments, the light sensor array is configured to generate an event coordinate corresponding to the position of the scintillation event based at least in part on the determined crystal element within which the scintillation event occurs and the determined position of the scintillation event along the third direction.

In various embodiments, a system for detecting a three-dimensional position of a scintillation event converting a radiation into a light includes a crystal pair and a light sensor pair. In some examples, the crystal pair includes a first crystal element and a second crystal element. In certain examples, the first crystal element and the second crystal element are arranged side-by-side along a first direction. In various examples, the first crystal element and the second crystal element extend along a third direction between a first end and a second end. In some examples, the first crystal element and the second crystal element are configured to receive the radiation entered from the second end. In certain examples, the crystal pair is optically coupled to a light bridge at the second end extending and bridging light along the first direction. In various examples, the first crystal element and the second crystal element are optically coupled for the light along the first direction through only the light bridge. In some examples, the light sensor pair includes a first light sensor corresponding to the first crystal element and a second light sensor corresponding to the second crystal element. In various examples, the first light sensor and the second light sensor are arranged side-by-side along the first direction.

In certain embodiments, the scintillation event has a corresponding event coordinate (e.g., x, y, z), which can be determined based at least in part on determining which crystal element (e.g., providing x, y) within which the scintillation event occurs and determining a position (e.g., providing z) of the scintillation event along the third direction. In some examples, if multiple scintillation events are determined with multiple corresponding event coordinates, determining the direction of the traveling radiation (e.g., gamma radiation) within the crystals is based at least in part on the depths of the event coordinates along the third direction.

In certain embodiments, an optical shield (e.g., optical separator) is configured to allow transmission of a first radiation (e.g., gamma radiation) but block transmission of a second radiation (e.g., visible light). In some examples, an optical shield (e.g., optical separator) arranged between two crystal elements is configured to block transmission of the second radiation (e.g., visible light) at least in the direction perpendicular to the interface of the two crystal elements. In various examples, an optical shield (e.g., optical separator) being optically transparent for a radiation (e.g., gamma radiation) when traveling between the two crystal elements indicates that the optical shield allows the radiation to transmit therethrough from one crystal element to another. In certain examples, an optical shield (e.g., optical separator) configured to shield a radiation (e.g., visible light) indicates that the optical shield is configured to block transmission of the radiation therethrough, such as at an interface between two crystal elements.

In certain embodiments, systems and/or methods of the present disclosure provide crystal and detector arrangements such that crystals may share detectors such that a detector may be shared between crystal groups. In certain examples, systems and/or methods of the present disclosure allows a detector signal to indicate not only detection of photoactivity, but also positioning among multiple crystal groups. In certain examples, systems and/or methods of the present disclosure does not sacrifice encoding in one direction in the plane of a photodetector array to provide encoding perpendicular to the plane. In certain examples, systems and/or methods of the present disclosure allows the crystals in one direction to be unequal to the extent of the photodetector.

Figure 18:
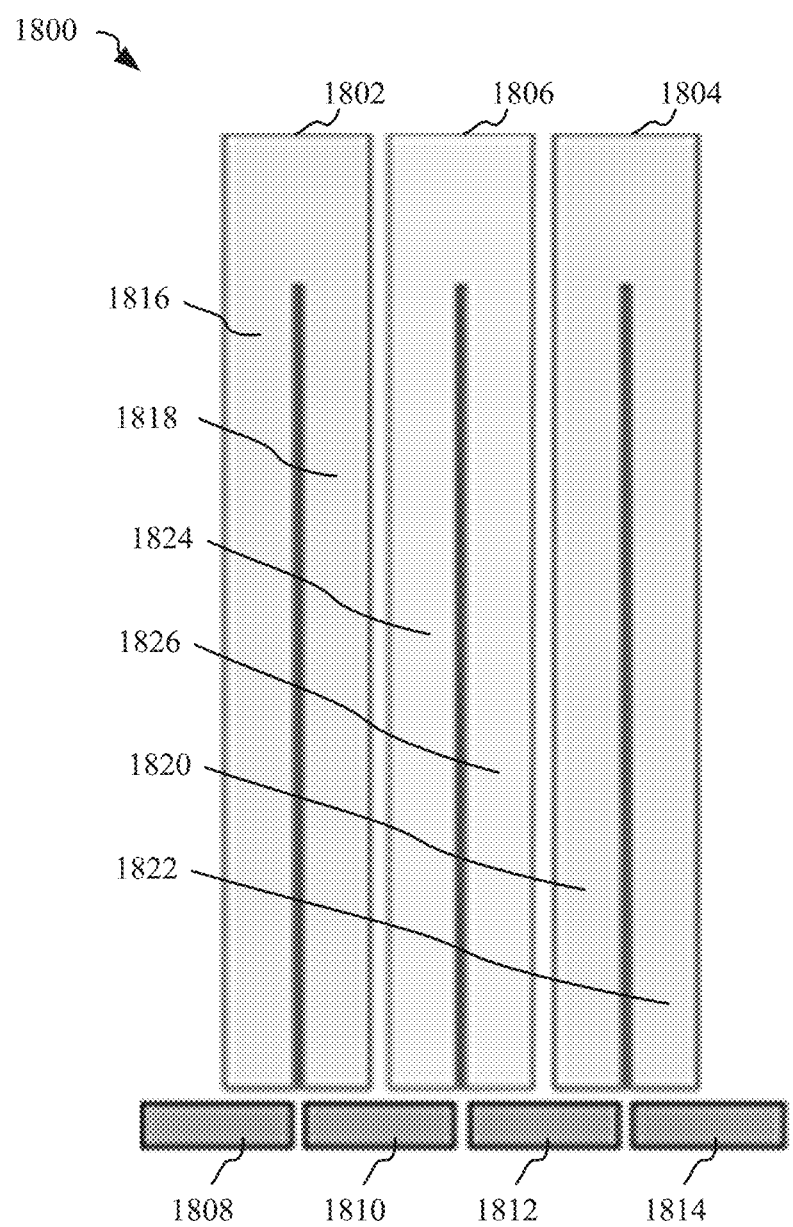
FIG. 18 is a simplified diagram showing a crystal group according to some embodiments of the present disclosure.

FIG. 18 is a simplified diagram showing a crystal group according to some embodiments of the present disclosure. This diagram is merely an example, which should not unduly limit the scope of the claims. One of ordinary skill in the art would recognize many variations, alternatives, and modifications. In various embodiments, to reduce size of crystal elements without sacrificing detector capabilities, the systems and/or methods of the present disclosure allows size reduction of crystal elements in at least one direction such that within a group of photodetectors, the original crystals cover half of the original area. In some examples, the systems and/or methods of the present disclosure includes additional crystal elements disposed at the gap at the uncovered haft such that those inserted additional crystal elements share photodetectors with its neighboring crystal elements. As such, a photodetector may provide a readout associated with more than just one crystal element, but two or more crystal elements. In some examples, systems and methods of the present disclosure provides photodetector sharing, such as in a quadrant-sharing manner such that each photodetector occupies a quadrant of a crystal couple. For example, each photodetector occupies a half of a crystal element of a crystal couple. As depicted in FIG. 18, three crystal element pairs may share two photodetector pairs, such that the center crystal element pair is shared between the two detector pairs. In some examples, photodetector 1808 and photodetector 1810 belongs to a first detector pair and correspond to a first crystal element pair 1802. In some examples, photodetector 1812 and photodetector 1814 belongs to a second detector pair and correspond to a second crystal element pair 1806. In some examples, photodetector 1808 of the first photodetector pair covers crystal element 1816 of crystal pair 1802. In some examples, photodetector 1814 of the second photodetector pair covers crystal element 1822 of crystal pair 1804. In some examples, photodetector 1810 of the first photodetector pair covers not only crystal element 1818 of crystal pair 1802, but also crystal element 1824 of crystal pair 1806. In some examples, between the crystal pairs 1802, 1804, and 1806, the interface may include a gap or an optical shield (e.g., optical separator). In some examples, the crystal pairs 1802, 1804, 1806 are of the similar or same size. In some examples, photodetector 1812 of the second photodetector pair covers not only crystal element 1820 of crystal pair 1804, but also crystal element 1826 of crystal pair 1806.

Figure 19:
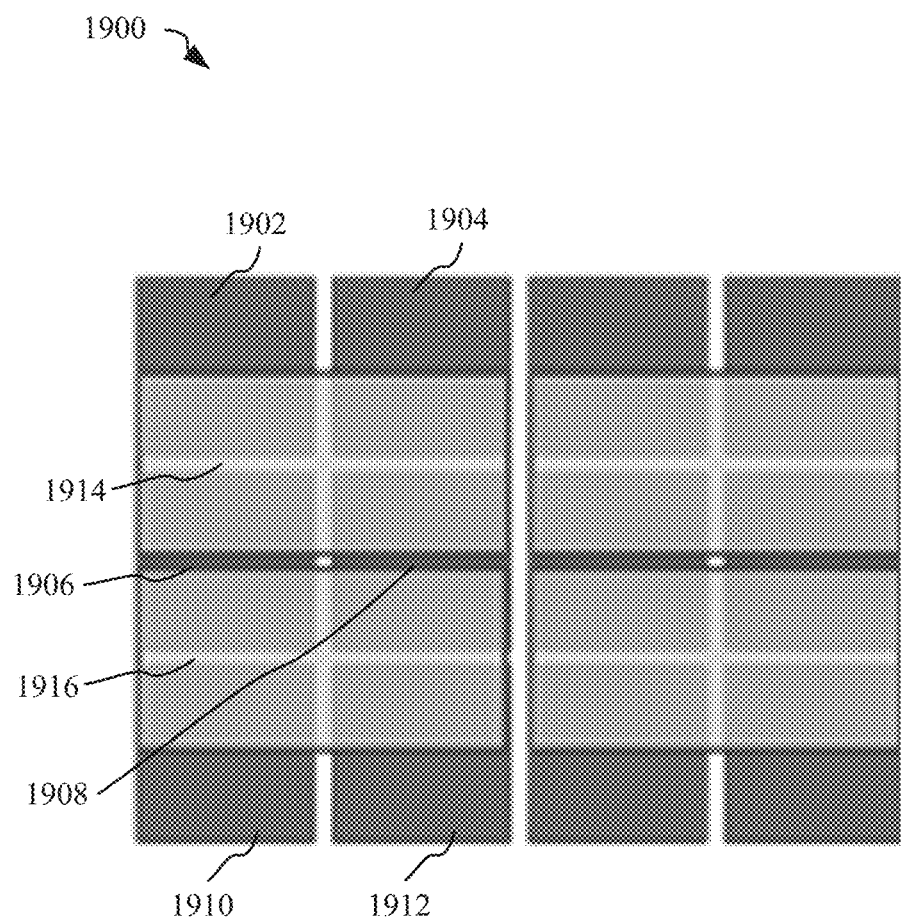
FIG. 19 is a simplified diagram showing a crystal array according to some embodiments of the present disclosure.

FIG. 19 is a simplified diagram showing a crystal array according to some embodiments of the present disclosure. This diagram is merely an example, which should not unduly limit the scope of the claims. One of ordinary skill in the art would recognize many variations, alternatives, and modifications. As depicted, photodetectors may be shared in at least one direction. In some examples, systems and/or methods of the present disclosure may detect photon interaction in either of the original crystal elements may produce a single record (e.g., measured by a single corresponding photodetector), whereas interactions in a shared crystal element may produce two records (e.g., measured by two neighboring photodetectors). As depicted in FIG. 19, a crystal array may be arranged on top of a shared grid of photodetectors. As shown, the crystal array may include a first crystal pair 1914 and a second crystal pair 1916, where the first crystal pair 1914 is arranged on photodetectors 1902, 1904, 1906, and 1908, and the second crystal pair 1916 is arranged on photodetectors 1906, 1908, 1910, and 1912. In some examples, photodetectors 1902, 1904, 1910, and 1912 each correspond to a single crystal pair, such as a single crystal element of a crystal pair. In some examples, photodetector 1906 is shared by the first crystal pair 1914 and the second crystal pair 1916, such as shared by a first crystal element of the first crystal pair 1914 and a first crystal element of the second crystal pair 1916. In some examples, photodetector 1908 is shared by the first crystal pair 1914 and the second crystal pair 1916, such as shared by a second crystal element of the first crystal pair 1914 and a second crystal element of the second crystal pair 1916.

Figure 20:
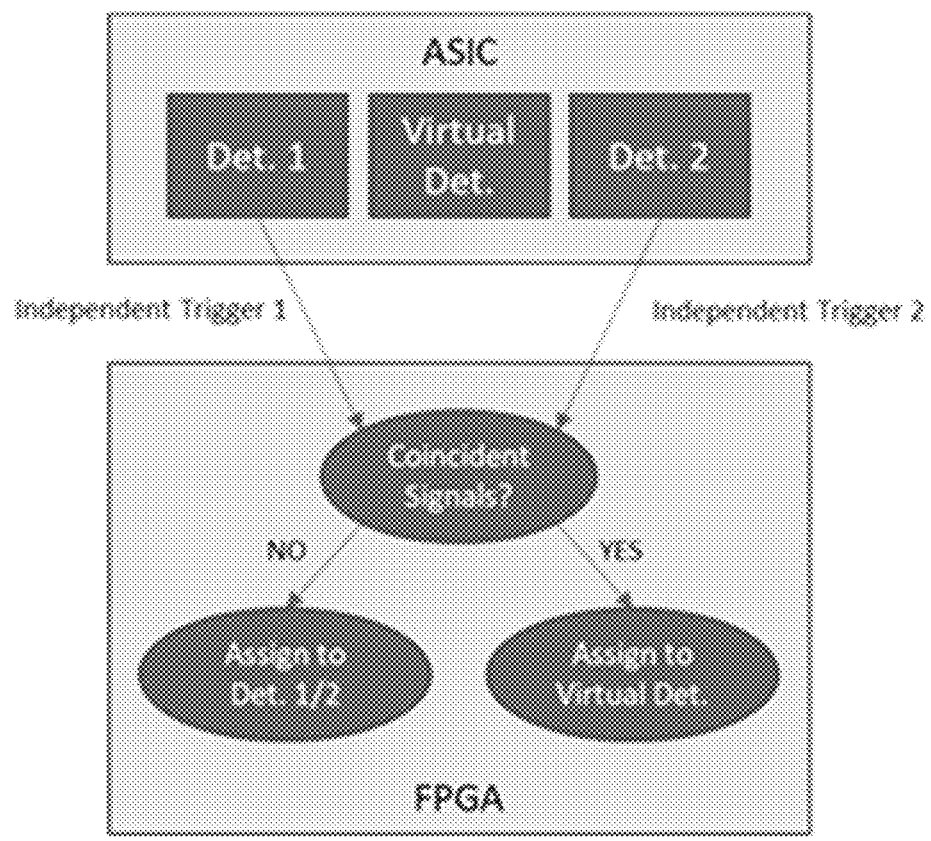
FIG. 20 is a simplified diagram showing a method for determining a detector for signal assignment.

FIG. 20 is a simplified diagram showing a method for determining a detector for signal assignment. This diagram is merely an example, which should not unduly limit the scope of the claims. One of ordinary skill in the art would recognize many variations, alternatives, and modifications. In certain examples, systems and/or methods of the present disclosure may adapt firmware and/or software for recognizing triggers from neighboring photodetectors which originate from a single shared crystal element. In some examples, processing of a shared detector signal includes using coincident triggers to identify events from a virtual detector. In some examples, systems and/or methods of the present disclosure may, such as via an application-specific integrated circuit (ASIC), receiving a first trigger and a second trigger, such as triggers recorded by neighboring photodetectors. In some examples, systems and/or methods of the present disclosure may, such as via a field-programmable gate array (FPGA), determining whether the first trigger and the second trigger are coincident signals. In various examples, if the signals are determined to be non-coincident, a light activity is assigned to the crystal pairs corresponding to the first photodetector and the second photodetector. In various examples, if the signals are determined to be coincident, a light activity is assigned to a shared crystal pair corresponding to a virtual detector (e.g., shared between two photodetectors).

In some examples, systems and/or methods of the present disclosure enables crystal element size to be reduced by a factor of two or more, such as without increase in light sharing, increase in channel density, or loss of encoding in any other direction. In certain examples, systems and/or methods of the present disclosure enables the realization of depth-encoding crystal elements at a clinical scale with a single-ended readout configuration and currently available electronics (e.g., photodetectors).

According to an aspect of the present disclosure, a PET detector may include a crystal array and a single-end readout structure. The crystal array may include a plurality of crystal elements. The plurality of crystal elements may be arranged along a first direction and a second direction so as to define a plurality of crystal groups along the first direction. Each of the plurality of crystal groups may include at least two crystal elements of the plurality of crystal elements. Each of the plurality of crystal elements may include a first end and a second end and may extend along a third direction from the first end to the second end. A photon-sensor array optically coupled with the crystal array. At least one pair of neighboring crystal groups of the plurality of crystal groups may include a first optical separator and a second optical separator. The first optical separator of a first length may locate between the crystal groups of the at least one pair of neighboring crystal groups, the first length being along the third direction. The second optical separator of a second length may locate between two neighboring crystal elements of a crystal group of the at least one pair of neighboring crystal groups, the second length being along the third direction. The first length of the first optical separator may be equal to or greater than the second length of the second optical separator.

In some embodiments, the photon-sensor array forms a single-end read-out structure, and the photon-sensor array may include a plurality of photon-sensors configured to receive photons emitted from the first ends of the plurality of crystal elements.

In some embodiments, each photon-sensor of the photon-sensor array may be optically coupled with one or more crystal elements of the plurality of crystal elements.

In some embodiments, the detector may include one or more third optical separators. Each of the one or more third optical separators may locate between two neighboring crystal elements along the second direction.

In some embodiments, at least one of the first optical separator, the second optical separator, or the one or more third optical separators may include at least one of a reflective film, a reflective foil, or a reflective coating.

In some embodiments, the first optical separator extends from the first end of one of the plurality of crystal elements to the second end of the one of the plurality of crystal elements.

In some embodiments, the second length of the second optical separator may be equal to or greater than a half of a length of at least one of the two neighboring crystal elements between which the second optical separator is located, the length of the crystal element being along the third direction.

In some embodiments, at least one of the first optical separator or second optical separator may extend, along the third direction, from the first end of at least one of two neighboring crystal elements between which the at least one of the first or second optical separator is located.

In some embodiments, at least one crystal group of the plurality of crystal groups, the second ends of the at least two crystal elements may be integrated into a single end.

In some embodiments, the first optical separator extends from the first end of one of the plurality of crystal elements to the second end of the one of the plurality of crystal elements.

According to another aspect of the present disclosure, a computer-implemented method may include one or more of the following operations performed by at least one processor. The method may include obtaining output information of at least two photon-sensors. The at least two photon-sensors may be optically coupled with one crystal group of a PET detector. The output information may correspond to a photon gamma interaction in the crystal group. The method may also include determining, based on the output information, a position of the photon gamma interaction within the crystal group.

In some embodiments, the method may also include identifying, in the crystal group, a target crystal element in which the photon gamma interaction occurs based on the output information.

In some embodiments, the method may also include determining a depth of the photon gamma interaction within the target crystal element based on the output information.

In some embodiments, the output information of the at least two photon-sensors may include an energy detected by each of the at least two photon-sensors. The method may also include determining a total energy detected by the at least two photon-sensors based on the energy detected by each of the at least two photon-sensors. The method may further include determining the position of the photon gamma interaction within the crystal group based on the energy detected by each of the at least two photon-sensors and the total energy.

According to another aspect of the present disclosure, a computer-implemented method may include one or more of the following operations performed by at least one processor. The method may include obtaining output information of a plurality of photon-sensor groups. Each of the plurality of photon-sensor groups may include at least two photon-sensors and being optically coupled to a crystal group of a PET detector. The output information may correspond to a photon gamma interaction in the plurality of crystal groups. The method may also include determining a plurality of candidate positions of the photon gamma interaction in the plurality of crystal groups based on the output information. Each of the plurality of candidate positions may correspond to one of the plurality of crystal groups and may include a candidate depth of the photon gamma interaction within the corresponding crystal group. The method may further include determining that an inter crystal scatter (ICS) occurs within the plurality of crystal groups based on the output information. The method may further include designating, among the plurality of candidate positions, the candidate position with the smallest candidate depth as a position of the photon gamma interaction.

According to still another aspect of the present disclosure, a PET detector may include a plurality of detector rings arranged along an axial direction of the detector. Each of the plurality of detector rings may include a plurality of crystal elements. The plurality of crystal elements may define a plurality of crystal groups arranged along the axial direction of the detector. Each of the plurality of crystal groups may include at least two crystal elements that belong to at least two individual detector rings. Each of the plurality of crystal elements may include a proximal end and a distal end with respect to a central axis of the detector and may extend along an extension direction from its distal end to its proximal end. At least a pair of neighboring crystal groups of the plurality of crystal groups may include a first optical separator and a second optical separator. The first optical separator of a first length may locate between the crystal groups of the at least one pair of neighboring crystal groups, the first length being along the extension direction of at least one crystal element of the at least one pair of neighboring crystal groups. The second optical separator of a second length may locate between two neighboring crystal elements of a crystal group of the at least one pair of neighboring crystal groups, the second length being along the extension direction of the at least one crystal element of the at least one pair of neighboring crystal groups. The first length of the first optical separator may be equal to or greater than the second length of the second optical separator.

In some embodiments, at least one detector ring may include a plurality of photon-sensors configured to receive photons emitted from respective distal ends of the plurality of crystal elements of the at least one detector ring.

In some embodiments, each photon-sensor of the plurality of photon-sensors may be optically coupled with one or more crystal elements of the at least one detector ring.

In some embodiments, at least one detector ring may include a third optical separator located between each pair of neighboring crystal elements of the at least one detector ring.

According to still another aspect of the present disclosure, a computer-implemented method may include one or more of the following operations performed by at least one processor. The method may include obtaining output information of at least two photon-sensors. Each photon-sensor of the at least two photon-sensors may be optically coupled with one or more of crystal elements that belong to a crystal group of a PET detector. The output information may correspond to a photon gamma interaction in the crystal group.

In some embodiments, the method may also include determining, based on the output information, a position of the photon gamma interaction within the crystal group.

In some embodiments, the method may also include identifying, among the crystal elements optically coupled to the at least two photon-sensors, a target crystal element where the photon gamma interaction occurs based on the output information.

In some embodiments, the method may also include determining a depth of the photon gamma interaction within the target crystal element based on the output information.

In some embodiments, the output information of the at least two photon-sensors may include an energy detected by each of the at least two photon-sensors, the method may also include determining a total energy detected by the at least two photon-sensors based on the energy detected by each of the at least two photon-sensors. The method may further include determining the position of the photon gamma interaction within the crystal group based on the energy detected by each of the at least two photon-sensors and the total energy.

According to still another aspect of the present disclosure, a PET detector may include a crystal array and a single-end read-out structure. The crystal array may include a plurality of crystal elements, the plurality of crystal elements being arranged along a first direction and a second direction so as to define a plurality of crystal groups along the first direction. Each of the plurality of crystal groups may include at least two crystal elements of the plurality of crystal elements. Each of the plurality of crystal elements may include a first end and a second end and may extend along a third direction from the first end to the second end. The single-end read-out structure may include a photon-sensor array optically coupled with the crystal array. At least one crystal group of the plurality of crystal groups may include an optical window configured to allow a light transmission between the at least two crystal elements of the at least one crystal group, so that a photon excited by an photon gamma interaction in a first crystal element of the at least one crystal group can travel into a second crystal element of the at least one crystal group through the second end of the first crystal element, the optical window, and the second end of the second crystal element.

In some embodiments, the optical window of the at least one crystal group may include an optical separator and a light transmission medium. For each of the at least two crystal elements of the at least one crystal group, the optical separator may mount on each side surface of the crystal element that faces a neighboring crystal element of the crystal element along the first direction. A length of the optical separator may equal to a length of at least one of the crystal element or the neighboring crystal element, the length of the optical separator and the length of the at least one of the crystal element or the neighboring crystal element being along the third direction. The light transmission medium may cover the second ends of the at least two crystal elements of the at least one crystal group. Each side surface of the light transmission medium that faces a neighboring crystal group of the at least one crystal group may be coated with a light reflective material.

In some embodiments, the light transmission medium may be glass.

In some embodiments, the photon-sensor array may include a plurality of photon-sensors configured to receive photons emitted from the first ends of the plurality of crystal elements.

In various embodiments, a system for detecting a three-dimensional position of a scintillation event converting a radiation into a light includes a crystal array including a plurality of crystal elements arranged at least along a first direction and a second direction, and a light sensor array including a plurality of light sensors arranged at least along the first direction and the second direction. In some examples, the plurality of crystal elements extends along a third direction between a first end and a second end. In some examples, the plurality of crystal elements is arranged into a plurality of crystal pairs. In certain examples, each of the plurality of crystal pairs is optically coupled to one light bridge at the second end extending and bridging light along the first direction. In various examples, each of the plurality of crystal pairs includes two crystal elements. In some examples, the two crystal elements in each crystal pair are arranged side-by-side along the first direction and optically coupled for the light along the first direction through only the one light bridge coupled to each crystal pair. In certain examples, each light bridge is optically shielded for the light along the second direction. In various examples, the plurality of crystal pairs is arranged side-by-side along at least the second direction. In some examples, each of the plurality of crystal pairs is optically coupled for the light in the second direction with at least a neighboring crystal pair only through two light tunnels. In certain examples, each light tunnel of the two light tunnels is optically shielded for the light along the first direction. In various examples, each of the two light tunnels optically couples one crystal element of each crystal pair with one crystal element of a neighboring crystal pair for the light in the second direction. In some examples, the plurality of light sensors is arranged into a plurality of light sensor pairs. In certain examples, each of the plurality of light sensor pairs includes two light sensors. In various examples, the two light sensors in each light sensor pair are arranged side-by-side along the first direction. In some examples, one light sensor pair of the plurality of light sensor pairs includes a first light sensor and a second light sensor. In certain examples, one crystal pair of the plurality of crystal pairs includes a first crystal element and a second crystal element. In various examples, the first light sensor corresponds to the first crystal element and the second light sensor corresponds to the second crystal element.

In various embodiments, a system for detecting one or more three-dimensional positions of one or more scintillation events converting a radiation into a light includes a crystal array including a plurality of crystal elements arranged in crystal rows along a first direction and in crystal columns along a second direction, and a light sensor array including a plurality of light sensors arranged in light sensor rows along the first direction and in light sensor columns along the second direction. In some examples, the plurality of crystal elements extends along a third direction between a first end and a second end. In some examples, one crystal row of the crystal rows includes one or more crystal pairs along the first direction. In certain examples, one crystal pair of the one or more crystal pairs includes a first crystal element and a second crystal element. In various examples, one light sensor row of the light sensor rows includes one or more light sensor pairs along the first direction. In some examples, one light sensor pair of the one or more light sensor pairs includes a first light sensor and a second light sensor. In certain examples, the first light sensor corresponds to the first crystal element. In various examples, the second light sensor corresponds to the second crystal element. In some examples, the one light sensor pair is configured to determine whether the scintillation event occurs within the first crystal element or within the second crystal element and/or determine the position of the scintillation event along the third direction. In certain examples, one crystal column of the crystal columns includes multiple crystal elements along the second direction. In various examples, one light sensor column of the light sensor columns includes multiple light sensors along the second direction. In some examples, the one light sensor column corresponds to the one crystal column. In certain examples, the one light sensor column is configured to determine within which crystal element of the multiple crystal elements the scintillation event occurs.

In various embodiments, a system for detecting a three-dimensional position of a scintillation event converting a radiation into a light includes a crystal pair and a light sensor pair. In some examples, the crystal pair includes a first crystal element and a second crystal element. In certain examples, the first crystal element and the second crystal element are arranged side-by-side along a first direction. In various examples, the first crystal element and the second crystal element extend along a third direction between a first end and a second end. In some examples, the first crystal element and the second crystal element are configured to receive the radiation entered from the second end. In certain examples, the crystal pair is optically coupled to a light bridge at the second end extending and bridging light along the first direction. In various examples, the first crystal element and the second crystal element are optically coupled for the light along the first direction through only the light bridge. In some examples, the light sensor pair includes a first light sensor corresponding to the first crystal element and a second light sensor corresponding to the second crystal element. In various examples, the first light sensor and the second light sensor are arranged side-by-side along the first direction.

In various embodiments, a system for detecting a three-dimensional position of a scintillation event converting a radiation into light includes: a crystal array including a plurality of crystal elements arranged at least along a first direction and a second direction, the plurality of crystal elements extending along a third direction between a first end and a second end, the crystal array including a plurality of light bridges at the second end and a plurality of light tunnels at the first end; and a light sensor array including a plurality of light sensors arranged at least along the first direction and the second direction. In some examples, the plurality of crystal elements is arranged into a plurality of crystal pairs; each of the plurality of crystal pairs optically coupled to one light bridge of the plurality of light bridges at the second end extending and bridging light along the first direction; each of the plurality of crystal pairs includes two crystal elements; and the two crystal elements in each crystal pair are arranged side-by-side along the first direction and optically coupled for the light along the first direction through the one light bridge coupled to each crystal pair. In some examples, the plurality of light sensors is arranged into a plurality of light sensor pairs at the first end and configured to detect light converted from the radiation entered from the second end; each of the plurality of light sensor pairs includes two light sensors; and the two light sensors in each light sensor pair are arranged side-by-side along the first direction. In some examples, a first crystal pair of the plurality of crystal pairs corresponds to a first light sensor pair of the plurality of light sensor pairs; a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair. In some examples, the system is configured according to FIG. 1, FIG. 12A, FIG. 12B, FIG. 13, FIG. 14A, FIG. 14B FIG. 18, FIG. 19, and/or FIG. 20.

In some embodiments, each light bridge of the plurality of light bridges is optically shielded for the light along the second direction. In some examples, the plurality of crystal pairs is arranged side-by-side along at least the second direction. In some examples, each of the plurality of crystal pairs is optically coupled for the light in the second direction with at least a neighboring crystal pair through two light tunnels of the plurality of light tunnels. In some examples, each light tunnel of the two light tunnels is optically shielded for the light along the first direction. In some examples, each light tunnel of the two light tunnels optically couples one crystal element of each crystal pair with one crystal element of a neighboring crystal pair for the light in the second direction. In some examples, each crystal element of the plurality of crystal elements is bounded by a plurality of optical shields extending along the third direction, the plurality of optical shields configured to shield at least the light.

In some embodiments, the plurality of optical shields includes a first optical shield arranged at an interface between two neighboring crystal pairs of the plurality of crystal pairs along the first direction. In some examples, the first optical shield extends from the first end to the second end to optically shield the two neighboring crystal pairs along the first direction.

In some embodiments, the plurality of optical shields includes a second optical shield arranged at an interface between the first crystal element and the second crystal element included in the one crystal pair of the plurality of crystal pairs. In some examples, the second optical shield extends from the first end towards the second end until reaching the light bridge optically coupling the first crystal element and the second crystal element.

In some embodiments, the plurality of optical shields includes a third optical shield arranged at an interface between two neighboring crystal pairs of the plurality of crystal pairs along the second direction. In some examples, the third optical shield extends from the second end towards the first end until reaching the light tunnel optically coupling the two neighboring crystal pairs along the second direction.

In some embodiments, the light bridge optically coupling the two crystal elements in each crystal pair is an internal light bridge configured to be optically transparent for the light when traveling between the two crystal elements.

In some embodiments, the light bridge optically coupling the two crystal elements in each crystal pair is an external light bridge configured to create an optical interface for the light when traveling between the two crystal elements.

In some embodiments, the light bridge optically coupling the two crystal elements in each crystal pair comprises a scintillation material or a transmitting material.

In some embodiments, the first direction is orthogonal to the second direction, first direction is orthogonal to the third direction, and the second direction is orthogonal to the third direction.

In some embodiments, the first direction is nonlinear and is along at least part of a circle.

In some embodiments, the plurality of crystal elements is polished at the second end.

In various embodiments, a system for detecting one or more three-dimensional positions of one or more scintillation events for converting a radiation into light includes: a crystal array including: a plurality of crystal elements arranged in crystal rows along a first direction and in crystal columns along a second direction, the plurality of crystal elements extending along a third direction between a first end and a second end; and a plurality of light bridges at the second end and a plurality of light tunnels at the first end; and a light sensor array including a plurality of light sensors arranged in light sensor rows along the first direction and in light sensor columns along the second direction, the plurality of light sensors arranged at the first end and configured to detect light converted from the radiation entered from the second end. In some examples, each crystal row of the crystal rows includes one or more crystal pairs along the first direction; each crystal pair of the one or more crystal pairs optically coupled to one light bridge of the plurality of light bridges at the second end extending and bridging light along the first direction each crystal pair of the one or more crystal pairs includes a first crystal element and a second crystal element; the first crystal element and the second crystal element are optically coupled for the light along the first direction through the one light bridge coupled to each crystal pair; each light sensor row of the light sensor rows includes one or more light sensor pairs along the first direction; each light sensor pair of the one or more light sensor pairs includes a first light sensor and a second light sensor. In some examples, each light sensor pair is configured to: determine whether the scintillation event occurs within the first crystal element or within the second crystal element; and determine the position of the scintillation event along the third direction. In some examples, a first crystal pair of the one or more crystal pairs corresponds to a first light sensor pair of the one or more light sensor pairs; a second crystal pair of the one or more crystal pairs corresponds to a second light sensor pair of the one or more light sensor pairs; and a third crystal pair of the one or more crystal pairs corresponds to the first light sensor pair and the second light sensor pair such that a scintillation event in the third crystal pair is detected by both the first light sensor pair and the second light sensor pair. In some examples, the system is configured according to FIG. 1, FIG. 12A, FIG. 12B, FIG. 13, FIG. 14A, FIG. 14B FIG. 18, FIG. 19, and/or FIG. 20.

In some embodiments, the first light sensor is configured to obtain a first energy; the second light sensor is configured to obtain a second energy; and each light sensor pair is configured to determine whether the position of a scintillation event is within the first crystal element or within the second crystal element based at least in part on the first energy and the second energy.

In some embodiments, each light sensor pair is further configured to determine the position of the scintillation event along the third direction based at least in part on the first energy and the second energy by: determining the location of the scintillation event to be in the first crystal element if the first energy is greater than the second energy; and determining the location of the scintillation event to be in the second crystal element if the first energy is less than the second energy.

In some embodiments, the first light sensor is configured to obtain a first energy; the second light sensor is configured to obtain a second energy; and each light sensor pair is configured to determine the position of the scintillation event along the third direction based at least in part on the first energy and the second energy.

In some embodiments, each light sensor pair is further configured to determine the position of the scintillation event along the third direction by: calculating an energy ratio based at least in part on the first energy and the second energy; and determining the position of the scintillation event along the third direction based at least in part on a look-up-table.

In some embodiments, each light sensor pair is further configured to determine the position of the scintillation event along the third direction by: calculating an energy ratio based at least in part on the first energy and the second energy; and determining the position of the scintillation event along the third direction based at least in part on a distance ratio between a first path and a second path, the first path being from the position of the scintillation event to the first light sensor, the second path being from the position of the scintillation event to the second light sensor.

In some embodiments, the crystal array includes a first crystal pair and a second crystal pair; the light sensor array includes a first light sensor pair and a second light sensor pair; the first light sensor pair is configured to determine a first three-dimensional position of a first scintillation event within the first crystal pair, the first three-dimensional position includes a first depth along the third direction from the second end; the second light sensor pair is configured to determine a second three-dimensional position of a second scintillation event within the second crystal pair, the second three-dimensional position includes a second depth along the third direction from the second end; and the first light sensor pair and the second light sensor pair are configured to: determine the first scintillation event occurs before the second scintillation event in response to the first depth being smaller than the second depth; and determine the first scintillation event occurs after the second scintillation event in response to the first depth being larger than the second depth.

In some embodiments, the light sensor array is configured to generate an event coordinate corresponding to the position of the scintillation event based at least in part on the determined crystal element within which the scintillation event occurs and the determined position of the scintillation event along the third direction.

In various embodiments, a system for detecting a three-dimensional position of a scintillation event converting a radiation into light includes: a crystal array including a plurality of crystal pairs arranged at least along a first direction and a second direction, each crystal pair of the plurality of crystal pairs including a first crystal element and a second crystal element, the crystal array including a plurality of light bridges at the second end and a plurality of light tunnels at the first end; and a light sensor array including a plurality of light sensor pairs at the first end and configured to detect light converted from the radiation entered from the second end. In some examples, for each crystal pair: the first crystal element and the second crystal element arranged side-by-side along the first direction; the first crystal element and the second crystal element extending along a third direction between a first end and a second end; the first crystal element and the second crystal element configured to receive the radiation entered from the second end; the crystal pair being optically coupled to one light bridge of the plurality of the light bridges at the second end extending and bridging light along the first direction; and the first crystal element and the second crystal element being optically coupled for the light along the first direction through the one light bridge. In some examples, a first crystal pair of the plurality of crystal pairs corresponds to a first light sensor pair of the plurality of light sensor pairs; a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair. In some examples, the system is configured according to FIG. 1, FIG. 12A, FIG. 12B, FIG. 13, FIG. 14A, FIG. 14B FIG. 18, FIG. 19, and/or FIG. 20.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A system for detecting a three-dimensional position of a scintillation event converting a radiation into light, the system comprising:
    a crystal array including a plurality of crystal elements arranged at least along a first direction and a second direction, the plurality of crystal elements extending along a third direction between a first end and a second end, the crystal array including a plurality of light bridges at the second end and a plurality of light tunnels at the first end; and a light sensor array including a plurality of light sensors arranged at least along the first direction and the second direction;

wherein:
the plurality of crystal elements is arranged into a plurality of crystal pairs;
each of the plurality of crystal pairs optically coupled to one light bridge of the plurality of light bridges at the second end extending and bridging light along the first direction;
each of the plurality of crystal pairs includes two crystal elements;
the two crystal elements in each crystal pair are arranged side-by-side along the first direction and optically coupled for the light along the first direction through the one light bridge coupled to each crystal pair;

wherein:
the plurality of light sensors is arranged into a plurality of light sensor pairs at the first end and configured to detect light converted from the radiation entered from the second end;
each of the plurality of light sensor pairs includes two light sensors; and
the two light sensors in each light sensor pair are arranged side-by-side along the first direction;

wherein:
a first crystal pair of the plurality of crystal pairs corresponds to a first light sensor pair of the plurality of light sensor pairs;
a second crystal pair of the plurality of crystal pairs corresponds to a second light sensor pair of the plurality of light sensor pairs; and
a third crystal pair of the plurality of crystal pairs corresponds to the first light sensor pair and the second light sensor pair such that a scintillation event in the third crystal pair is detected by both the first light sensor pair and the second light sensor pair.

2. The system of claim 1, wherein:
each light bridge of the plurality of light bridges is optically shielded for the light along the second direction;
the plurality of crystal pairs is arranged side-by-side along at least the second direction;
each of the plurality of crystal pairs is optically coupled for the light in the second direction with at least a neighboring crystal pair through two light tunnels of the plurality of light tunnels;
each light tunnel of the two light tunnels is optically shielded for the light along the first direction;
each light tunnel of the two light tunnels optically couples one crystal element of each crystal pair with one crystal element of a neighboring crystal pair for the light in the second direction;
each crystal element of the plurality of crystal elements is bounded by a plurality of optical shields extending along the third direction, the plurality of optical shields configured to shield at least the light.

3. The system of claim 2, wherein the plurality of optical shields includes a first optical shield arranged at an interface between two neighboring crystal pairs of the plurality of crystal pairs along the first direction, wherein the first optical shield extends from the first end to the second end to optically shield the two neighboring crystal pairs along the first direction.

4. The system of claim 2, wherein the plurality of optical shields includes a second optical shield arranged at an interface between the first crystal element and the second crystal element included in the one crystal pair of the plurality of crystal pairs, wherein the second optical shield extends from the first end towards the second end until reaching the light bridge optically coupling the first crystal element and the second crystal element.

5. The system of claim 2, wherein the plurality of optical shields includes a third optical shield arranged at an interface between two neighboring crystal pairs of the plurality of crystal pairs along the second direction, wherein the third optical shield extends from the second end towards the first end until reaching the light tunnel optically coupling the two neighboring crystal pairs along the second direction.

6. The system of claim 1, wherein the light bridge optically coupling the two crystal elements in each crystal pair is an internal light bridge configured to be optically transparent for the light when traveling between the two crystal elements.

7. The system of claim 1, wherein the light bridge optically coupling the two crystal elements in each crystal pair is an external light bridge configured to create an optical interface for the light when traveling between the two crystal elements.

8. The system of claim 1, wherein the light bridge optically coupling the two crystal elements in each crystal pair comprises a scintillation material or a transmitting material.

9. The system of claim 1, wherein the first direction is orthogonal to the second direction, first direction is orthogonal to the third direction, and the second direction is orthogonal to the third direction.

10. The system of claim 9, wherein the first direction is nonlinear and is along at least part of a circle.

11. The system of claim 1, wherein the plurality of crystal elements is polished at the second end.

12. A system for detecting one or more three-dimensional positions of one or more scintillation events for converting a radiation into light, the system comprising:
a crystal array including:
a plurality of crystal elements arranged in crystal rows along a first direction and in crystal columns along a second direction, the plurality of crystal elements extending along a third direction between a first end and a second end; and
a plurality of light bridges at the second end and a plurality of light tunnels at the first end; and
a light sensor array including a plurality of light sensors arranged in light sensor rows along the first direction and in light sensor columns along the second direction, the plurality of light sensors arranged at the first end and configured to detect light converted from the radiation entered from the second end;

wherein:
each crystal row of the crystal rows includes one or more crystal pairs along the first direction;
each crystal pair of the one or more crystal pairs optically coupled to one light bridge of the plurality of light bridges at the second end extending and bridging light along the first direction;
each crystal pair of the one or more crystal pairs includes a first crystal element and a second crystal element;
the first crystal element and the second crystal element are optically coupled for the light along the first direction through the one light bridge coupled to each crystal pair; and each light sensor row of the light sensor rows includes one or more light sensor pairs along the first direction;
each light sensor pair of the one or more light sensor pairs includes a first light sensor and a second light sensor;
wherein each light sensor pair is configured to:
determine whether the scintillation event occurs within the first crystal element or within the second crystal element; and
determine the position of the scintillation event along the third direction;
wherein:
a first crystal pair of the one or more crystal pairs corresponds to a first light sensor pair of the one or more light sensor pairs;
a second crystal pair of the one or more crystal pairs corresponds to a second light sensor pair of the one or more light sensor pairs; and
a third crystal pair of the one or more crystal pairs corresponds to the first light sensor pair and the second light sensor pair such that a scintillation event in the third crystal pair is detected by both the first light sensor pair and the second light sensor pair.

13. The system of claim 12, wherein:
the first light sensor is configured to obtain a first energy;
the second light sensor is configured to obtain a second energy; and
each light sensor pair is configured to determine whether the position of a scintillation event is within the first crystal element or within the second crystal element based at least in part on the first energy and the second energy.

14. The system of claim 13, wherein each light sensor pair is further configured to determine the position of the scintillation event along the third direction based at least in part on the first energy and the second energy by:
determining the location of the scintillation event to be in the first crystal element if the first energy is greater than the second energy; and
determining the location of the scintillation event to be in the second crystal element if the first energy is less than the second energy.

15. The system of claim 12, wherein:
the first light sensor is configured to obtain a first energy;
the second light sensor is configured to obtain a second energy; and
each light sensor pair is configured to determine the position of the scintillation event along the third direction based at least in part on the first energy and the second energy.

16. The system of claim 15, wherein each light sensor pair is further configured to determine the position of the scintillation event along the third direction by:
calculating an energy ratio based at least in part on the first energy and the second energy; and
determining the position of the scintillation event along the third direction based at least in part on a look-up-table.

17. The system of claim 15, wherein each light sensor pair is further configured to determine the position of the scintillation event along the third direction by:
calculating an energy ratio based at least in part on the first energy and the second energy; and
determining the position of the scintillation event along the third direction based at least in part on a distance ratio between a first path and a second path, the first path being from the position of the scintillation event to the first light sensor, the second path being from the position of the scintillation event to the second light sensor.

18. The system of claim 12, wherein:
the crystal array includes a first crystal pair and a second crystal pair;
the light sensor array includes a first light sensor pair and a second light sensor pair;
the first light sensor pair is configured to determine a first three-dimensional position of a first scintillation event within the first crystal pair, the first three-dimensional position includes a first depth along the third direction from the second end;
the second light sensor pair is configured to determine a second three-dimensional position of a second scintillation event within the second crystal pair, the second three-dimensional position includes a second depth along the third direction from the second end; and
the first light sensor pair and the second light sensor pair are configured to:
determine the first scintillation event occurs before the second scintillation event in response to the first depth being smaller than the second depth; and
determine the first scintillation event occurs after the second scintillation event in response to the first depth being larger than the second depth.

19. The system of claim 12, wherein the light sensor array is configured to generate an event coordinate corresponding to the position of the scintillation event based at least in part on the determined crystal element within which the scintillation event occurs and the determined position of the scintillation event along the third direction.

20. A system for detecting a three-dimensional position of a scintillation event converting a radiation into light, the system comprising:
a crystal array including a plurality of crystal pairs arranged at least along a first direction and a second direction, each crystal pair of the plurality of crystal pairs including a first crystal element and a second crystal element, the crystal array including a plurality of light bridges at the second end and a plurality of light tunnels at the first end; and
a light sensor array including a plurality of light sensor pairs at the first end and configured to detect light converted from the radiation entered from the second end;
wherein for each crystal pair:
the first crystal element and the second crystal element arranged side-by-side along the first direction;
the first crystal element and the second crystal element extending along a third direction between a first end and a second end;
the first crystal element and the second crystal element configured to receive the radiation entered from the second end;
the crystal pair being optically coupled to one light bridge of the plurality of the light bridges at the second end extending and bridging light along the first direction; and
the first crystal element and the second crystal element being optically coupled for the light along the first direction through the one light bridge;
wherein:
a first crystal pair of the plurality of crystal pairs corresponds to a first light sensor pair of the plurality of light sensor pairs;

a second crystal pair of the plurality of crystal pairs corresponds to a second light sensor pair of the plurality of light sensor pairs; and a third crystal pair of the plurality of crystal pairs corresponds to the first light sensor pair and the second light sensor pair such that a scintillation event in the third crystal pair is detected by both the first light sensor pair and the second light sensor pair.

\* \* \* \* \*